US008394623B2

(12) United States Patent
Stewart

(10) Patent No.: US 8,394,623 B2
(45) Date of Patent: Mar. 12, 2013

(54) **METHODS AND COMPOSITIONS COMPRISING *TRICHODERMA ATROVIRIDE* FOR THE BIOLOGICAL CONTROL OF SOIL BORNE PLANT PATHOGENS AND PROMOTING PLANT GROWTH**

(75) Inventor: Alison Stewart, Christchurch (NZ)

(73) Assignee: Lincoln University (NZ)

( * ) Notice: Subject to any disclaimer, the term of this patent is extended or adjusted under 35 U.S.C. 154(b) by 282 days.

(21) Appl. No.: 12/867,012

(22) PCT Filed: Feb. 13, 2009

(86) PCT No.: PCT/NZ2009/000015
§ 371 (c)(1),
(2), (4) Date: Aug. 10, 2010

(87) PCT Pub. No.: WO2009/102222
PCT Pub. Date: Aug. 20, 2009

(65) Prior Publication Data
US 2011/0009260 A1    Jan. 13, 2011

Related U.S. Application Data

(60) Provisional application No. 61/028,569, filed on Feb. 14, 2008.

(51) Int. Cl.
*C12N 1/14* (2006.01)
*C12N 1/00* (2006.01)
*A01N 63/04* (2006.01)
*A01N 63/00* (2006.01)

(52) U.S. Cl. .............. 435/256.7; 435/254.1; 435/945; 424/93.5; 504/117

(58) Field of Classification Search .................. None
See application file for complete search history.

(56) References Cited

U.S. PATENT DOCUMENTS

| | | | |
|---|---|---|---|
| 4,489,161 A | 12/1984 | Papavizas |
| 4,713,342 A | 12/1987 | Chet et al. |
| 4,748,021 A | 5/1988 | Chet et al. |
| 4,915,944 A | 4/1990 | Chet et al. |
| 5,084,272 A | 1/1992 | Speakerman et al. |
| 5,238,690 A | 8/1993 | Elad et al. |
| 5,260,213 A | 11/1993 | Harman et al. |
| 5,266,316 A | 11/1993 | Elad et al. |
| 5,418,165 A | 5/1995 | McBeath |
| 5,780,023 A | 7/1998 | McLaughlin et al. |
| 5,882,914 A | 3/1999 | Semenza |
| 6,753,295 B1 | 6/2004 | Sasaki |
| 6,808,917 B1 | 10/2004 | Johnson |
| 6,890,530 B2 | 5/2005 | Hermosa Prieto et al. |
| 7,070,984 B2 | 7/2006 | Munoz |
| 2002/0103083 A1 | 8/2002 | Harman |
| 2004/0067851 A1 | 4/2004 | Misumi et al. |
| 2004/0261578 A1 | 12/2004 | Harman et al. |

FOREIGN PATENT DOCUMENTS

| | | |
|---|---|---|
| EP | 1876232 A1 | 1/2008 |
| JP | 11-225745 A | 8/1999 |
| WO | WO-2004054365 A1 | 7/2004 |
| WO | WO-2007110686 A2 | 10/2007 |
| WO | WO-2007116245 A1 | 10/2007 |

OTHER PUBLICATIONS

Steward et al. "How Much of Biocontrol is Enough"; In: Biological Control: a Global Perspective; eds C. Vincent, M.S. Goettel and G. Lazarovits. 2007, pp. 185-196.*
Chen et al. "Effects of *Trichoderma atroviride* on Pythium damping off of pea". Phytopathology. 1993, vol. 83, No. 12, p. 137, abstract A146.*
McBeath et al. "Evaluation of *Trichoderma atroviride* in controlling *Rhizoctonia solani* of potato under potato field conditions in Montana". Phytopathology. 1995, vol. 85, No. 10, p. 1153, abstract 307.*
"AmPac Inc.—Cucumber Research Report", [online]. (c) 2003 AmPac Biotech. {retrieved on Oct. 4, 2012]. Retrieved from the Internet: <URL: http://www.ampacbiotech.net/research/cucumber.htm>, (2003), 1 pg.
"AmPac Inc.—Grape Research Report", [online]. (c) 2003 AmPac Biotech. [retrieved on Oct. 4, 2012]. Retrieved from the Internet: <UR: http://www.ampacbiotech.net/research/grape.htm>, (2003), 2 pgs.
"Biocontrol Activities of *Trichoderma atroviride—T. atroviride* Slides", [online]. (c) 2003 AmPac Biotech. [retrieved on Oct. 4, 2012]. Retrieved from the Internet: <URL: http://www.ampacbiotech.net/research/trich/trichslide.html>, (2003), 6 pgs.
"Cotton Health Improvement by Plant Helper—Cotton Slides", [online]. (c) 2003 AmPac Biotech. [retrieved on Oct. 4, 2012]. Retrieved from the Internet: <URL: http://www.ampacbiotech.net/research/cotton/cottonslide.html>(2003), 5 pgs.
"Flower Health Improvement by Plant Helper—Flower Sldes", [online]. (c) 2003 AmPac Biotech. [retrieved Oct. 4, 2012]. Retrieved from the Internet: <URL: http://www.ampacbiotech.net/research/flowers/flowerslide.html>, (2003), 2 pgs.
"Ginseng Health Improvement by Plant Helper—Ginseng Slides", [online]. (c) 2003 AmPac Biotech. [retrieved Oct. 4, 2012]. Retrieved from the Internet: <URL: http://www.ampacbiotech.net/research/ginseng/ginsengslide.html>, (2003), 5 pgs.
"Grape Health Improvement by Plant Helper—Grape Slides", [online]. (c) 2003 AmPac Biotech. [retrieved on Oct. 4, 2012]. Retrieved from the Internet: <URL: http://ampacbiotech.net/research/grape/grapeslide.html>, (2003), 2 pgs.
"Pepper Health Improvement by Plant Helper—Pepper Slides", [online]. (c) 2003 AmPac Biotech. [retrieved Oct. 4, 2012]. Retrieved from the Internet: <URL: http://www.ampacbiotech.net/research/pepper/pepperslide.html>, (2003), 2 pgs.
"Potato Health Improvement by Plant Helper—Potato Slides", [online]. (c) 2003 AmPac Biotech. [retrieved Oct. 4, 2012]. Retrieved from the Internet: <URL: http://www.ampacbiotech.net/research/potato/potatoslide.html>, (2003), 4 pgs.

(Continued)

*Primary Examiner* — Vera Afremova
(74) *Attorney, Agent, or Firm* — Schwegman Lundberg & Woessner, P.A.

(57) ABSTRACT

The present invention relates to *Trichoderma atroviride* strains and their use as biological control agents or plant growth promoters. Methods and compositions for biological control of soil borne plant pathogens, and increasing plant yield using *T. atroviride* are also provided.

20 Claims, 1 Drawing Sheet

OTHER PUBLICATIONS

"Turfgrass Health Improvement by Plant Helper—Turfgrass Slides", [online]. (c) 2003 AmPac Biotech. [retrieved Oct. 4, 2012]., (2003), 4 pgs.

Kandula, D. R. W., et al., "Improving Pasture Establishment and Yield With a *Trichoderma* Bio-Inoculant", Proceedings, 16th Biennial Australasian Plant Pathology Society Conference Back to Basics: Managing Plant Disease, (2007), p. 40.

McBeath, J. H., "Biocontrol and Growth Promotion with Cold Tolerant *Trichoderma*", [online]. The IPM Practitioner, XXXIII(2), [retrieved Oct. 4, 2012]. Retrieved from the Internet: <URL: http://www.ampacbiotech.net/Articles%20&%20Pubs/ipm1.jpg>, (Feb. 2001), 6 pgs.

McBeath, J. H., "Biological management of snow mold", [online]. [archived on Jun. 15, 2004]. Retrieved from the Internet: <http://web.archive.org/web/20040615192659/http://www.gcsaa.org/gcm/2003/mar03/PDFs/Biological.pdf>, (2003), 3 pgs.

McBeath, J. H., et al., "Control of Seed-borne Late Blight on Pre-cut Potatoe Seed with *Trichoderma atroviride*", [online]. (c) 2003 AmPac Biotech. [retrieved Oct. 4, 2012]. Retrieved from the Internet: <URL: http://www.ampacbiotech.net/research/pot1.html>, (2003), 9 pgs.

McBeath, J. H., et al., "Effects of *Trichoderma atroviride* on the Root System of *Panax quinquefolius*", [online]. (c) 2003 AmPac Biotech. [retrieved on Oct. 4, 2012]. Retrieved from the Internet: <URL: http://www.ampacbiotech.net/research/ging1.html>, (2003), 9 pgs.

McBeath, J. H., et al., "Evaluation of in-Furrow Soil Application of *Trichoderma atroviride* on the Germination and Growth of Cotton seedlings", [online]. [retrieved Oct. 4, 2012]. Retrieved from the Internet: <URL: http://www.ampacbiotech.net/research/cotton1.jpg>, (2012), 5 pgs.

McBeath, J. H., et al., "Growth and Yield Responses of Potatoes to Formulated *Trichoderma atroviride* Seed-piece Treatment", Plant Pathology and Biotechnology Lab, University of Fairbanks, (Feb. 24, 2011), 6 pgs.

McBeath, J. H., "Snow Mold-Plant-Antagonist Interactions: Survival of the Fittest Under Snow", [online]. [retrieved on Oct. 4, 2012]. Retrieved from the Internet: <URL: http://www.apsnet.org/publications/apsnetfeatures/Pages/snowmold.aspx>, (2002), 16 pgs.

McBeath, J. H., "*Trichoderma atroviride* (Cold Tolerant *Trichoderma*)", [online]. (c) 2003 AmPac Biotech. [retrieved on Oct. 4, 2012]. Retrieved from the Internet: <URL: http://www.ampacbiotech.net/Articles%20&%20Pubs/trich.html>, (2003), 10 pgs.

Talbott, C., "Professor makes grass truly greener", [online]. (c) 2003 AmPac Biotech. [retrieved on Oct. 4, 2012]. Retrieved from the Internet: <URL: http://www.ampacbiotech.net/Articles%20&%20Pubs/fairbanks.html>, (May 14, 2001), 1 pg.

McLean, K. L., et al., "Effect of Formulation on the Rhizosphere Competence and Biocontrol Ability of *Trichoderma atroviride* C52", Plant Pathology, 54(2), (2005), 212-218.

Monaco, C., et al., "Survival and Proliferation of *Trichoderma koningii* in alginate pills", World Journal of Microbiology and Biotechnology, 15(1), (1999), 123-125.

\* cited by examiner

METHODS AND COMPOSITIONS COMPRISING *TRICHODERMA ATROVIRIDE* FOR THE BIOLOGICAL CONTROL OF SOIL BORNE PLANT PATHOGENS AND PROMOTING PLANT GROWTH

RELATED APPLICATIONS

This application is a nationalization under 35 U.S.C. 371 of PCT/NZ2009/000015, filed Feb. 13, 2009 and published as WO 2009/102222 A1, on Aug. 20, 2009, which claimed priority under 35 U.S.C. 119(e) to U.S. Patent Application Ser. No. 61/028,569, filed Feb. 14, 2008; which applications and publication are incorporated herein by reference in their entirety.

FIELD OF THE INVENTION

This invention relates to novel *Trichoderma atroviride* and compositions containing same. Methods for the biological control of soil borne plant pathogens; and methods for increasing plant yield using *Trichoderma atroviride* are also provided.

BACKGROUND OF THE INVENTION

Plant disease represents a significant economic cost to modern agriculture. Current systems of agriculture often require one or a few crops or plant types to be grown over a large area. Such an ecologically unbalanced system is susceptible to disease.

Traditionally, control of plant pathogens such as fungi has been pursued through the use of chemical fungicides or pesticides. However, consumers are becoming increasingly concerned about chemical residues on plants and their effects on the environment. Moreover; pathogens are becoming increasingly resistant to available fungicides and pesticides.

Biological, control represents an alternative means of controlling plant disease which reduces dependence on chemicals. Such "natural" methods enjoy greater public acceptance, and may be more effective and sustainable than chemical control methods.

A wide range of biological control agents including bacteria, yeast and fungi have been investigated for use in controlling plant disease. One mechanism which has been demonstrated to be effective is the use of microbial antagonists such as *Trichoderma* and *Gliocladium* species to control plant pathogenic fungi, and to promote plant growth.

*Trichoderma* is a genus of fungi containing about 20 species of which many have been explored for their biocontrol and growth promotion potential. See for example U.S. Pat. No. 4,748,021, U.S. Pat. No. 4,713,342, U.S. Pat. No. 4,915,944, U.S. Pat. No. 5,084,272, U.S. Pat. No. 5,238,690, U.S. Pat. No. 5,260,213, U.S. Pat. No. 5,266,316, U.S. Pat. No. 5,882,914, U.S. Pat. No. 6,753,295, and U.S. Pat. No. 7,070,984. *Trichoderma harzianum* in particular is the active component in a number of commercially available products such as PlantShield®, and RootShield® Granules (Bioworks Inc, New York, USA) for suppression of root diseases and growth promotion. *Trichoderma viride* is an effective biocontrol agent against fusarium wilt in Chrysanthemum (U.S. Pat. No. 4,489,161). *Trichoderma viride* is also the active component in the commercially available product Trieco® (Ecosense Labs, India), and in the bio-fungicide Sentinel® (Agrimm Technologies Ltd, New Zealand), which is used for control of *Botrytis Cinerea* on grapes and tomatoes. More recently, combinations of *Trichoderma* with other fungal and/or bacterial antagonists have been explored for use as broader spectrum biocontrol agents and for plant growth promotion. See for example U.S. Pat. No. 6,808,917, U.S. Pat. No. 6,890,530, US 2002/0103083, US 2004/0261578, WO 2004/054365, WO 2007/110686 and WO 2007/116245.

The efficacy of various *Trichoderma* species for biocontrol and growth promotion has also been discussed by Stewart et al, Australian Plant Pathology Society, Adelaide, 2007.

Despite extensive investigations into *Trichoderma* species for biocontrol and growth promotion, very few *Trichoderma* products are available for commercial use. None are available for use on pasture plants. This is primarily because of the complex interactions that take place in the soil or on plants between *Trichoderma* and other microorganisms, the environment, and the plant or plant root.

Therefore, while potential biocontrol and plant growth promotion agents with antagonistic characteristics can be found, they must be carefully screened for a range of traits relevant to their proposed use. These traits include plant pathogenicity, antagonistic activity and specificity, amenability to manipulation in delivery systems and formulations, and performance under fluctuating field conditions with target plants. Establishment and performance in the field is often the most difficult challenge to overcome. Any *Trichoderma* agent must be able to successfully establish and compete with the multitude of existing field microorganisms, in a way, which is not harmful to target plants. *Trichoderma* combination products present further challenges where all *Trichodermas* selected for use in a combination must be compatible and not out compete each other under field conditions. Accordingly, there is still a need for new *Trichoderma* species for use as biocontrol and/or growth promotion agents which address these issues.

The applicants have now identified a number of new *Trichoderma atroviride* that are highly effective as biocontrol agents and/or growth promotants either alone or in combination.

An object of the invention is therefore to provide novel *Trichoderma atroviride* strains useful as biocontrol agents or as growth promotants or as both. Another object is to provide a composition comprising at least one of the novel *Trichoderma atroviride* strains of the invention, a combination of all strains of the invention, or all four strains identified herein; or at least to provide the public with a useful choice.

BRIEF DESCRIPTION OF THE DRAWINGS

The invention will now be described with reference to figures in the accompanying drawings which.

SUMMARY OF THE INVENTION

Figure 1:
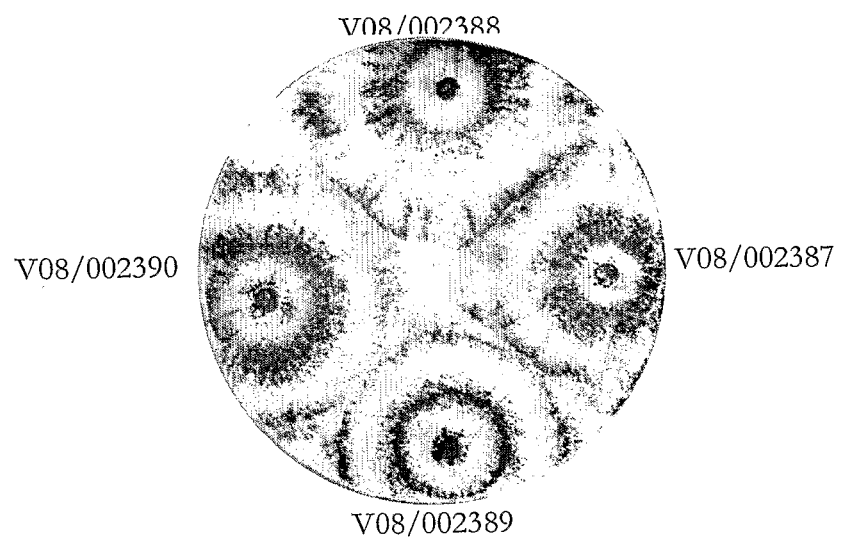
FIG. 1. Compatibility of Pasture Seed Additive *Trichoderma atroviride* isolates. Mycelial plugs were inoculated to opposite sides of a potato-dextrose agar (PDA) plate and cultured at 20° C. under alternating light/dark conditions for 4 days.
Figure 2:
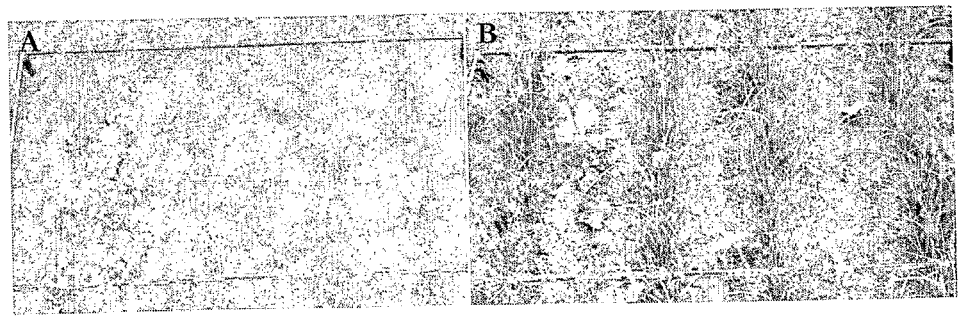
FIG. 2. Pasture Seed Additive Field Trial 3 (Lincoln University) 5 weeks after sowing. A. Untreated control block. B. PSA treated block.

Accordingly, in one aspect the invention provides a composition comprising in a reproductively viable form and amount, at least one strain of *Trichoderma atroviride* selected from:
(a) *Trichoderma atroviride* NMI No. V08/002387;
(b) *Trichoderma atroviride* NMI No. V08/002389; and
(c) *Trichoderma atroviride* NMI No. V08/002390 and an agriculturally acceptable carrier, diluent or adjuvant.

In one embodiment, the composition comprises all of strains (a), (b) and (c).

In one embodiment the composition further comprises *Trichoderma atroviride* strain NMI No. V008/002388 in a reproductively viable form and amount.

In another embodiment the invention provides a composition comprising, in a reproductively viable faun and amount, each of the following strains:

(a) *Trichoderma atroviride* NMI No. V08/002387;
(b) *Trichoderma atroviride* NMI No. V08/002389;
(c) *Trichoderma atroviride* NMI No. V08/002390; and
(d) *Trichoderma atroviride* NMI No. V08/002388

The compositions of the invention are effective against soil borne plant pathogens and are useful to promote plant growth, yield or both.

Preferably, any strains used in the compositions are present in the form of reproductively viable spores.

The invention also provides isolated strains or biologically pure cultures of *Trichoderma atroviride* strains NMI No. V08/002387, NMI No. V08/002389 and NMI No. V08/002390.

The compositions of the invention may be in a liquid form but are more usually in solid form. Solid forms include pellets or prills.

The preferred compositions are also preferred for the other aspects of the invention.

In another aspect, the invention provides a method for controlling soil borne plant pathogens on a seed or plant, or in soil, pasture, or turf the method comprising applying to said seed, plant, soil, pasture, or turf, a composition of the invention.

In another aspect, the invention provides a method for controlling soil borne plant pathogens on a seed or plant, or in soil, pasture or turf, the method comprising applying to said seed, plant, soil, pasture or turf one or more *T. atroviride* selected from *T. atroviride* Nos. V08/002387, V08/002388, V08/002389, and V08/002390.

In another aspect, the invention provides a method for increasing plant yield, the method comprising applying to a seed, plant, soil, pasture or turf, a composition of the invention.

The invention also provides a method for increasing plant yield, the method comprising applying to a seed, plant, pasture, turf, or soil one or more *T. atroviride* selected from *T. atroviride* Nos V08/002387, V08/002388, V08/002389, and V08/002390.

In the methods of the invention the seed or plants are grown in the usual way, and grazed or harvested as required.

Definitions

The term "biological control agent" as used herein refers to agents which act as antagonists of one or more soil borne plant pathogens. Antagonists may take a number of forms. In one form, the biological control agent may out compete the pathogen for available nutrients and/or space of the host plant. In another form the biological control agent may render the environment unfavourable for the pathogen. Accordingly, the antagonist mechanisms include but are not limited to antibiosis, mycoparasitism, nutrient competition and physical displacement.

The terms "control", "controlling", "biocontrol" or "biological control" are used interchangeably herein to refer to the reduction of the amount of inoculum or disease-producing activity of a pathogen accomplished by or through the use of one or more *Trichoderma*, microorganism(s) or compositions of the invention. Generally comprehended is the prevention or reduction of infection by soil borne plant pathogenic fungi, or inhibition of the rate or extent of such infection. Curative treatment is also contemplated.

The term "comprising" as used in this specification means "consisting at least in part of". When interpreting each statement in this specification that includes the term "comprising", features other than that or those prefaced by the term may also be present. Related terms such as "comprise" and "comprises" are to be interpreted in the same manner.

The term "effective amount" as used herein means an amount effective to protect against, delay, reduce, stabilise, improve or treat soil borne plant pathogenic fungal infection in a plant and/or elicit a plant growth promotion effect.

The term "plant" as used herein encompasses not only whole plants but also extends to plant parts, cuttings and plant products. For example, roots, leaves, seeds, stems, callus tissue, and fruit.

The term "plant growth promoter" as used herein broadly refers to an agent which increases the total plant yield measured as dry weight mass in kilograms per plant, hectare or similar. The terms "promote plant growth", plant growth promoter" and "growth promoter" should be similarly understood.

The term "vessel" as used herein retains its common meaning and refers to any object having the capacity to hold or contain something. A bioreactor may also refer to a device or system meant to grow cells or tissues in the context of cell culture.

The term "yield" refers to the total plant yield measured as dry weight mass in kilograms per plant, per hectare or similar.

The effect of a composition comprising a combination of *Trichoderma* strains of the present invention is expected to be a synergistic effect. According to the present invention a combination is defined as affording a synergistic effect if the effect is superior, as measured by the plant yield, the inhibition of disease caused by soil borne plant pathogens, or the time to disease progression, compared to that achievable on treatment with one of or the most effective *Trichoderma* strain in the combination treatment at its conventional application level. For example, the effect of the combination treatment is synergistic if the effect is superior to the effect achievable with one of the *Trichoderma* alone. Further, the effect of the combination treatment is synergistic if a beneficial effect is obtained in a group of plants that does not respond (or responds poorly) to one of the *Trichoderma* alone.

DETAILED DESCRIPTION OF THE INVENTION

In one aspect, the present invention is directed to strains of *Trichoderma atroviride* having efficacy against soil borne plant pathogenic fungi. The strains are therefore useful as biocontrol agents. The strains also act as plant growth promoters to increase plant yield.

*Trichoderma atroviride* are fast growing saprophytic fungi commonly found in soils around the world. Identifying morphological characteristics of *T. atroviride* are provided in example 2.

The new *T. atroviride* strains have all been deposited in the National Measurement Institute Laboratories (NMI), Suakin Street, Pymble, New South Wales, Australia on 31 Jan. 2008 according to the Budapest Treaty for the purposes of patent procedure. The isolates have been accorded deposit numbers NMI No. V08/002387, NMI No. V08/002389, and NMI No. V08/002390 respectively.

A known *T. atroviride* strain previously available from Lincoln University, New Zealand has also been deposited for the purpose of patent procedure under the Budapest Treaty on 31 Jan. 2008 at NMI. This isolate has been accorded deposit number NMI No. V08/002388

Details of the isolation and selection process employed to obtain the isolates are set out in the Examples.

The applicants have been the first to provide *T. atroviride* strains NMI No. V08/002387, NMI No. V08/002389, and NMI No. V08/002390 in isolated form.

Accordingly, in one aspect the invention provides *T. atroviride* NMI No. V08/002387

In another aspect the invention provides *T. atroviride* NMI No. V08/002389

In another aspect the invention provides *T. atroviride* NMI No. V08/002390

Also provided are *T. atroviride* strains having the identifying characteristics of the *T. atroviride* strains of the invention.

In one embodiment the *T. atroviride* strains of the invention are isolated. In another embodiment, the strains are provided in the form of a biologically pure culture.

The strains of the invention are effective as either biological control agents or plant growth promoters which increase plant yield, or as both. They demonstrate the ability to survive formulation and application protocols, are compatible in combination (see FIG. 1), rapidly colonise soils and plants, and suppress growth of plant pathogenic fungi, particularly soil borne pathogens including *Rhizoctonia*, *Sclerotinia*, *Pythium* and *Fusarium* (see Table 3 in Example 1). These soil borne pathogens are particularly problematic in pastures commonly causing damping off and root rots pre- or post-emergence in plants.

*T. atroviride* strain NMI No. V08/002387 is particularly effective against *R. solani* and *S. trifoliorum*.

*T. atroviride* strain NMI No. V08/002389 is particularly effective against *R. solani* and *P. ultimum*.

*T. atroviride* strain NMI No. V08/002390 is particularly effective against *P. ultimum*.

*T. atroviride* strain NMI No. V08/002388 is effective against *R. solani*, *S. trifoliorum*, *F. culmorum*, and *F. oxysporum*.

All four atroviride strains above are useful for increasing plant yield. Strains NMI No. V08/2389 and NMI V08/002390 are particularly effective for increasing plant yield.

The present invention also provides a composition comprising in a reproductively viable form and amount, at least one strain of *Trichoderma atroviride* selected from:
   (a) *Trichoderma atroviride* NMI No. V08/002387;
   (b) *Trichoderma atroviride* NMI No. V08/002389; and
   (c) *Trichoderma atroviride* NMI No. V08/002390
and an agriculturally acceptable carrier, diluent, or adjuvant.

The composition may include combinations of any two or more strains of the *T. atroviride* of the invention. That is a composition comprising *T. atroviride* NMI No. V08/002387 and *T. atroviride* NMI No. V08/002389, a composition comprising *T. atroviride* No. V08/002387 and *T. atroviride* NMI No. V08/002390, and a composition comprising *T. atroviride* NMI No. V08/002389 and *T. atroviride* NMI No. V08/002390. In one embodiment the composition comprises all three strains of the *T. atroviride* invention.

In a further embodiment the compositions of the invention also include *T. atroviride* strain NMI No. V08/002388 in a reproductively viable form and amount. This strain is particularly effective against *R. solani*.

Accordingly, in one embodiment the invention provides a composition comprising, in a reproductively viable form and amount, each of the following strains:
   (a) *Trichoderma atroviride* NMI No. V08/002387;
   (b) *Trichoderma atroviride* NMI No. V08/002389;
   (c) *Trichoderma atroviride* NMI No. V08/002390; and
   (d) *Trichoderma atroviride* NMI No. V08/002388

Effective concentrations of *T. atroviride* as biological control agents and/or growth promoters in the composition may vary depending on the form the *T. atroviride* is used in, physiological condition of the plant; type, concentration and degree of pathogen infection; temperature; season; humidity; soil type; pH; stage in the growing season; age of the plant; number and type of conventional fertilizers, fungicides and pesticides being applied and plant treatments (for example pruning, grazing and irrigation). All factors may be taken into account in formulating the composition using known art protocols.

The strain(s) of *T. atroviride* included must be in a reproductively viable form. For most purposes the *T. atroviride* is desirably incorporated into the composition in the form of spores or conidia. The concentration of the spores in the composition will depend on the utility to which the composition is put. Typical concentration ranges for each of the *T. atroviride* in the composition is from $1 \times 10^3$ to $1 \times 10^{14}$, commonly $1 \times 10^6$ to $1 \times 10^{11}$ or $1 \times 10^5$ to $1 \times 10^8$, or $1 \times 10^6$ to $1 \times 10^7$ colony forming units (CFU) per gram for solid compositions, and per millilitre for liquid compositions.

*T. atroviride* may be prepared for use in the compositions of the invention using standard static drying and liquid fermentation techniques known in the art. Growth is commonly effected in a bioreactor.

A bioreactor refers to any device or system that supports a biologically active environment. As described herein a bioreactor is a vessel in which microorganisms including *T. atroviride* can be grown. A bioreactor may be any appropriate shape or size for growing the microorganisms. A bioreactor may range in size and scale from 10 ml to litre's to cubic meters and may be made of stainless steel or any other appropriate material as known and used in the art. The bioreactor may be a batch type bioreactor, a fed batch type or a continuous-type bioreactor (e.g., a continuous stirred reactor). For example, a bioreactor may be a chemostat as known and used in the art of microbiology for growing and harvesting bacteria. A bioreactor may be obtained from any commercial supplier, for example, GEA Process Engineering Inc. (Maryland, USA). See also Bioreactor System Design, J. Asenjo and J. Merchuk, CRC Press, 1995.

For small scale operations, a batch bioreactor may be used, for example, to test and develop new processes, and for processes that cannot be converted to continuous operations.

Microorganisms grown in a bioreactor may be suspended or immobilized. Growth in the bioreactor is generally under aerobic conditions at suitable temperatures and pH for growth. Typical growth temperatures are from 15 to 30° C., 15 to 28° C., 20 to 30° C. or 15 to 25° C. The pH of the growth medium is usually slightly acidic to neutral at pH 4.0 to 7.0, or 4.5 to 6.5, or pH 5.0 to 6.0.

Growth medium may be any known art medium suitable for culture of *Trichoderma* species, such as potato dextrose broth, molasses yeast extract or corn steep liqueur. The strains when grown under these conditions generally produce spores within days. The spores may be harvested using conventional washing, filtering or sedimentary techniques such as centrifugation, or may be harvested dry using a cyclone system, for example a MycoHarvester MKV (MycoHarvester, Bateman, Berks, UK). Spores can be used immediately or stored under chilled conditions (1° C. to 10° C., 1 to 7° C., 2 to 4° C. or 2° C.), or may be freeze dried. Preferably, chilled spores are used within 2 weeks of harvest. Dried spore preparations can be used for as long as they remain reproductively viable usually up to 2 years. Generally dried spores are used within 25 weeks.

The composition of the invention may be in liquid or solid form. The spore containing growth medium discussed above is a liquid. This liquid can be used per se for example as a dip or spray to inoculate seeds, plants, soils, pastures, or turf. Seeds coated with the liquid composition may be subsequently dried and stored for future use. Accordingly, in another aspect the invention provides seeds coated with a composition of the invention.

The liquid composition may be further formulated with an agriculturally acceptable diluent such as water to form a spray, foam, drench, slurry, gel, dip or paste and combined with co-formulants or nutrient amendments such as seaweed.

The liquid composition may further comprise a broad range of additives such as surfactants, wetting agents, humectants, stickers, spreaders, stabilisers, and penetrants to enhance activity, and stressing agents to improve spore vigour. Examples of stressing agents include potassium chloride, sodium chloride, glycerol and glucose.

Additives may also include compositions which assist in maintaining microorganism viability in long term storage, for example unrefined corn oil and so called invert emulsions containing a mixture of oils and waxes on the outside and water, sodium alginate and conidia on the inside. Examples of surfactants, spreaders, penetrants, and stickers include Fortune®, Pulse®, C-Daxoil®, Codacide Oil®, D-C. Tate®, Supamet Oil, Bond®, Citowett® and Freeway®. Examples of suitable compositions including carriers, preservatives, surfactants and wetting agents, spreaders, and nutrients are provided in U.S. Pat. No. 5,780,023 incorporated herein by reference. Where selected for inclusion, common agricultural surfactants, such as Tween (available from Rohm & Haas) are desirably included in the composition according to known protocols. It is important that any additives used are present in amounts that do not interfere with the effectiveness of the *T. atroviride*.

In one embodiment the composition is in solid form. This composition may be produced by drying of the liquid compositions of the invention. Alternatively, a solid composition useful herein may be produced by combining spores with an agriculturally acceptable carrier such as seed, lime, kaolin, maize chip, humate and diatomite or mixtures thereof. One preparation comprises a powdered form of the composition which may be dusted onto plants.

In one embodiment the solid composition is prepared in the form of pellets or prills using known art techniques. In one embodiment prill production involves coating *Trichoderma* in any appropriate rotary mixing bowl. For production of prills see for example, Monaco et al. 1999, Survival and Proliferation of *Trichoderma koningii* in alginate prills, World Jnl of Microbiol. and Biotechnol, Vol 15 (1) pp 123-125, and Concise Encyclopedia of Plant Pathology, P. Vidhyasekaran, The compositions of the invention, in whatever form may also include acidulants, alginates, mannans, glycerol, polysaccharides, cellulose, xylans, carageenans, nutrients, trace elements, minerals, proteins, fats, soluble carbohydrates, insoluble carbohydrates and vitamins, and additives to extend shelf life.

In one embodiment, the prill includes maize chip, diatomite, humate and nutrient mix. The nutrient mix contains soluble and insoluble carbohydrates, protein, fats and trace elements commonly employed in prills. The pellets or prills are particularly useful for sowing into new pastures or oversowing of older established pastures.

The compositions of the invention may also include other control or growth promotant organisms including other *Trichoderma* species and *Gliocladium* species, such as *T. harzianum* or *G. virens*, germination promoters, fungicides, additives and inert carriers as discussed above, provided they are compatible with the survival and growth of the *T. atroviride.*

Similarly, any of the carriers, diluents, adjuvants and additives used in the compositions of the invention should not be phytotoxic, or bacteriocidal.

In a further aspect, the present invention provides a method for controlling soil borne plant pathogenic fungi on a seed or plant, or in soil, pasture or turf, the method comprising applying to said seed, plant, soil, pasture, or turf, a composition of the invention.

In another embodiment of the method for controlling soil borne plant pathogenic fungi one or more *T. atroviride* selected from *T. atroviride* Nos. V08/002387, V08/002388, V08/002389, and V08/002390. are applied. In one embodiment all four *T. atroviride* are applied. The *T. atroviride* in one embodiment are in the form of a composition of the invention.

In one embodiment, a composition of the invention may be applied to seed as discussed above. In other embodiments a composition of the invention may be applied to seed or plants by spraying, dipping, rubbing, brushing and the like. In one embodiment, for application to soil, pastures, or turf, pellets or prills are sown into soil with seed, or oversown into pastures or turf with or without seed. In an alternate embodiment the *Trichoderma* strain(s) or compositions of the invention are applied to existing pastures or turf in the form of a wetable powder as a root drench.

Applications to soil, pasture or turf, may be once only, or repeated as required. Applications at different times in plant life cycles are also contemplated depending on the use contemplated. For example at harvest to delay post harvest attack by fungal pathogens on plants.

Commonly, the *Trichoderma* strain(s) or composition of the invention is applied to the soil before, at the same time, or after seed is planted to facilitate plant germination and growth. Application to existing plants such as pastures and turfs are also desirable using standard oversowing techniques preferably in good growing conditions at application rates of 2 to 40 kg/ha, 10 to 25 kg/ha, or 5 to 15 kg/ha. In one embodiment 10 kg/ha is applied. An annual application following seed sowing is contemplated for pastures and turf.

Plant pathogenic fungi which may be controlled using one or more of the *T. atroviride* above, or compositions of the invention include soil borne fungi. Particularly;

*Rhizoctonia* including *R. solani*

*Sclerotinia* including *S. trifoliorum*

*Pythium* including *P. ultimum* and

*Fusarium* including *F. culmorum*, and *F. oxysporum.*

These pathogens cause damping-off and root-rot of almost all the pasture species except *Sclerotinia trifoliorum* which is confined to clovers and lucerne.

The compositions can be used to treat or pretreat soils (including potting mixes), or seeds as opposed to direct plant application. Also encompassed are plants, soils and seeds treated with one or more *T. atroviride* strains, or a composition of the invention.

The compositions and *T. atroviride* strains can also be used in hydroponic systems including soilless bags, and rockwool.

A wide range of plants may be treated using the strains and compositions of the invention. Such plants include vegetable and arable crops, commonly brassicas (including canola, cabbage, and kale), cereals (including wheat, barley and maize), pasture plants and Lucerne (alfalfa) which are susceptible to disease caused by the pathogenic fungi discussed herein. In one embodiment the brassicas, cereals and pasture plants are forage plants. In another embodiment the brassicas, cereals and pasture plants are fit for human consumption. The strains and compositions of the invention have proven particularly effective in controlling soil borne pathogenic fungi affecting forage pasture plants including pasture and turf grass species.

Grasses are typically within the plant order Poales, and the family Poacea. Contemplated for treatment are grasses including Poa, Lolium, Dactylis, Festuca, Deschampsia, Agrostis, Axonopus, Paspalum, Phleum, Koelena, Gynodon, Zoysia, Buchlo, Eremchloa and Stentaphrumor, or mixtures thereof.

In one embodiment the strains and compositions of the invention are used to control said soil borne pathogenic fungi affecting pasture grasses. The pasture grasses are in one embodiment selected from the group consisting of ryegrass (*Lolium*) and fescue (*Festuca*) species, for example from the group consisting of *Lolium perenne* (perennial ryegrass) and *Festuca arundinacea* (tall fescue).

Other plants that may be usefully treated with the strains and compositions of the invention include other species of ryegrass and fescue, including, but not limited to *Lolium multiflorum* (Italian ryegrass), *Lolium hybridum* (hybrid ryegrass), *Lolium rigidum* (Wimerra grass), *Lolium temulentum* (darnel), *Festuca rubra* (red fescue) and *Festuca pratensis* (meadow fescue), species of *Phleum* such as *Phleum pratense* (Timothy); and species of *Plantago* such as *Plantago major* (Plantain).

Another common pasture plant amenable to treatment using the compositions and strains of the invention is clover (*Trifolium* species). Specifically contemplated for treatment are *Trifolium repens* (white clover) and *Trifolium pratense* (red clover).

The applicants have also found that the novel *Trichoderma* strains, strain V08/002388, and compositions of the invention can be used to increase plant yield as shown in the examples. Accordingly, in another aspect the invention provides a method for increasing plant yield, the method comprising applying to a seed, plant, pasture, turf or soil, a composition of the invention, or one or more *T. atroviride* selected from *T. atroviride* Nos V08/002387, V08/002388, V08/002389, and V08/002390. In one embodiment all four *T. atroviride* are applied. The *T. atroviride* in one embodiment are in the faun of a composition of the invention. Application techniques are as discussed above. The plant, seed, pasture or turf, may then be grown in any conventional way.

This method is particularly useful for the pasture and turf plants and mixtures thereof identified above.

The following non-limiting Examples are provided to illustrate the present invention and in no way limit the scope thereof. In the Examples, the term Pasture Seed Additive ("PSA") to refer to *Trichoderma* strain(s), or composition of the invention is used for convenience.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

Example 1

Process for Selection of Pasture Seed Additive Biocontrol Agents

Introduction

Many isolates of the fungal species *Trichoderma* have been well characterised as biocontrol agents of soil-borne plant diseases. At Lincoln University, over 200 strains of *Trichoderma* have been isolated and identified from New Zealand agricultural and horticultural environments. Selection of *Trichoderma* biocontrol agents (BCA) from within the Lincoln University restricted collection for the biocontrol application was initially achieved by dual culturing with the target pathogen. 102 isolates of *Trichoderma* spp. were screened against three soil-borne pasture pathogens (*Rhizoctonia solani*, *Sclerotinia trifoliorum* and *Pythium ultimum*) to identify candidates for incorporation into a Pasture Seed Additive. Potential *Trichoderma* spp. candidates were then screened in planta for compatibility, biocontrol activity and plant growth promotion using three pasture disease complexes (perennial ryegrass vs *R. solani*, red clover vs *S. trifoliorum* and white clover vs *P. ultimum*).

Methods

Isolate Descriptions

All isolates used in this study originated in New Zealand. *Trichoderma* isolates were identified to genus level on the basis of growth on *Trichoderma* Selective Medium (TSM) and to species level on the basis of colony and conidial morphology and taxonomic sequence analysis, which is standard practice for *Trichoderma* identification. Pathogen isolates were identified on the basis of morphology and infectivity of their respective hosts. Isolate designations are given in Table 1.

TABLE 1

Fungal isolates used in this study

| Species | Designation |
| --- | --- |
| *Trichoderma atroviride* | LU136, LU298, LU497, LU563, LU572, LU573, LU574, LU575, LU576, LU577, LU578, LU579, LU580, LU581, LU582, LU583, LU585, LU586, LU587, LU588, LU589, LU590, LU591, LU634, LU737, NMI No. V08/002387, NMI No. V08/002389, NMI No. V08/002390, NMI No. V08/002388 |
| *Trichoderma aureoviride* | LU498 |
| *Trichoderma hamatum* | LU565, LU592, LU593, LU594, LU595, LU740 |
| *Trichoderma fertile* | LU609, LU610, LU611, LU622, LU623 |
| *Trichoderma harzianum* | LU564, LU612, LU613, LU614, LU630, LU631, LU632, LU635, LU636, LU637, LU638, LU639, LU640, LU641, LU642, LU643 |
| *Trichoderma koningii* | LU506, LU507, LU508, LU509, LU566, LU713, LU738 |
| *Trichoderma virens* | LU540, LU547, LU549, LU555 |
| *Trichoderma viride* | LU570, LU606, LU608, LU615, LU616, LU618, LU619, LU620, LU644, LU645, LU646, LU647 |

TABLE 1-continued

Fungal isolates used in this study

| Species | Designation |
|---|---|
| *Trichoderma* spp. | LU501, LU502, LU503, LU504, LU505, LU596, LU604, LU605, KW1, KW2, KW3, KW4, KW5, KW6, KW7, KW8, KW9, Ashley Dene, Gorge, Temuka, Paparua, Waimakariri |
| *Rhizoctonia solani* | KW11 |
| *Sclerotinia trifoliorum* | KW12 |
| *Pythium ultimum* | KW13 |
| *Fusarium culmorum* | KW14 |
| *Fusarium oxysporum* | KW15 |

Dual Culture Plate Assays

Agar plugs from the colony margins of 2 day old cultures grown on potato-dextrose agar (PDA) were inoculated to PDA plates to evaluate inhibition of fungal growth. To each plate one *Trichoderma* isolate and one pathogen were inoculated to opposite sides of the agar and plates were incubated for 21 days at 20° C. under alternating light/dark (12 hour/12 hour) conditions. At the end of the incubation period plates were scored as follows:

A: Pathogen not inhibited when the two colonies meet and hyphae of the pathogen grows over *Trichoderma*

B1-B4: The growing margins of the two colonies meet, pathogen growth is inhibited and overgrown by the *Trichoderma* isolate.

B1: Pathogen severely inhibited. Heavy sporulation of *Trichoderma*

B2: Pathogen nearly covers half of the Petri-plate. *Trichoderma* sporulation moderate.

B3: Delayed and sparse sporulation of *Trichoderma*

B4: No sporulation of *Trichoderma*

C: The growing margins of the pathogen and *Trichoderma* meet and stop growing further D: Pathogen is inhibited at a distance leaving a zone of inhibition Pot Trials Based on the results of the plate assays, ten *Trichoderma* spp. isolates (LU540, LU547, LU634, LU644, LU713, LU740 NMI No. V08/002387, NMI No. V08/002389, NMI No. V08/002390 and NMI No. V08/002388) were selected from the dual culture plate assays for further analysis in pot trials analysing both growth promotion and disease protection. All trials were fully replicated and used a randomised block design. Each experiment ran for 7 weeks. Trial details were as follows:

Pot Trial 1: Growth promotion of perennial ryegrass in the absence of pathogen
   200 g potting mix was added to each pot
   40 perennial ryegrass (*Lolium perenne* cv. Embassy) seeds were sown per pot
   Treatments consisted of either potting mix without *Trichoderma* (8 replicates) or potting mix with one *Trichoderma* isolate (4 replicates)
   Seedling emergence, fresh shoot and dry root weights were recorded Pot Trial 2: Growth promotion of red clover in the absence of pathogen
   200 g potting mix was added to each pot
   40 red clover (*Trifolium pratense* cv. Montgomery Red) seeds were sown per pot
   Treatments consisted of either potting mix without *Trichoderma* (8 replicates) or potting mix with one *Trichoderma* isolate (4 replicates)
   Seedling emergence and fresh shoot weight were recorded Pot Trial 3: Growth promotion of perennial ryegrass in the presence of *R. solani*
   200 g potting mix was added to each pot
   40 perennial ryegrass (*Lolium perenne* cv. Embassy) were sown per pot
   Treatments consisted of either potting mix without *Trichoderma* (8 replicates), potting mix with *R. solani* KW11 (8 replicates) or potting mix with one *Trichoderma* isolate and *R. solani* KW11 (4 replicates)
   Wheat bran/*R. solani* inoculum was prepared as described in Example 2, and added to the potting mix at 0.5% w/w
   Seedling emergence, fresh shoot and dry root weights were recorded Pot Trial 4: Growth promotion of red clover and disease control in the presence of *S. trifoliorum*
   200 g potting mix was added to each pot
   40 red clover (*Trifolium pratense* cv. Montgomery Red) were sown per pot
   Treatments consisted of either potting mix without *Trichoderma* (8 replicates), potting mix with *S. trifoliorum* KW12 (8 replicates) or potting mix with one *Trichoderma* isolate and *S. trifoliorum* KW12 (4 replicates)
   Wheat bran/*S. trifoliorum* inoculum was prepared as described in Example 2, and added to the potting mix at 3% w/w
   Seedling emergence, fresh shoot weight and disease severity were recorded Pot Trial 5: Growth promotion of white clover and disease control in the presence of *P. ultimum*
   200 g potting mix was added to each pot
   40 white clover (*Trifolium repens* cv. Aran) were sown per pot
   Treatments consisted of either potting mix without *Trichoderma* (10 replicates), potting mix with *P. ultimum* KW13 (10 replicates) or potting mix with one *Trichoderma* isolate and *P. ultimum* KW13 (10 replicates)
   *P. ultimum* oospore inoculum was multiplied on sterile clover roots and added to the potting mix at 0.2% w/w
   Seedling emergence, shoot weight, percentage emerged seedlings showing disease and disease severity were recorded Statistical Analysis Disease severity was assessed using a 1-5 scale and all results analysed using simple ANOVA.

Results

Dual Culture Plate Assay

Of the 102 *Trichoderma* spp. isolates screened for biocontrol activity, 10 were identified as having good antagonistic and suppressive abilities against all four pathogens. Selection criteria also included vigorous growth and high sporulation capability. The ten potential biocontrol agents (BCAs) consisted of five isolates of *T. atroviride* (NMI No. V08/002387, NMI No. V08/002389, NMI No. V08/002390, NMI No. V08/002388 and LU634), two isolates of *T. virens* (LU540 and LU547) and one isolate each of *T. koningii* (LU713), *T. hamatum* (LU740) and *T. viride* (LU644) (Table 2).

TABLE 2

Dual-plate assay screening of 102 *Trichoderma* isolates against soil-borne pasture pathogens. Isolates selected for further study are highlighted

| Isolates | KW11 | KW12 | KW13 | KW14 | KW15 |
|---|---|---|---|---|---|
| *T. atroviride* | | | | | |
| LU136 | C | B1 | B4 | B2 | |
| LU298 | B2 | B1 | B4 | B1 | |
| LU497 | B1 | B2 | B4 | B1 | |
| LU563 | B2 | B2 | B4 | B1 | |
| LU572 | B2 | B1 | B4 | B1 | |
| LU573 | B2 | B2 | B4 | B1 | |
| LU574 | B2 | B2 | B4 | B1 | |
| LU575 | B3 | B1 | B4 | B2 | |
| LU576 | B4 | B4 | B4 | B4 | |
| LU577 | B2 | B2 | B4 | B2 | |
| LU578 | B1 | B3 | B4 | B1 | |
| LU579 | B2 | B2 | B4 | B2 | |
| LU580 | B2 | B2 | B4 | B1 | |
| LU581 | B2 | B2 | B4 | B1 | |
| LU582 | B2 | B2 | B4 | B1 | |
| LU583 | B2 | B2 | B4 | B1 | |
| LU585 | B2 | B2 | B4 | B1 | |
| LU586 | B1 | B2 | B4 | B1 | |
| LU587 | B2 | B2 | B4 | B1 | |
| LU588 | B2 | B2 | B4 | B1 | |
| LU589 | B2 | B2 | B4 | B1 | |
| LU590 | B2 | B2 | B4 | B1 | |
| LU591 | B1 | B2 | B4 | B1 | |
| LU634 | B1 | B1 | B4 | B1 | B1 |
| LU737 | B2 | B2 | B4 | B3 | B2 |
| NMI No. V08/002388 | B1 | B1 | B4 | B1 | B1 |
| NMI No. V08/002387 | B1 | B1 | B4 | B1 | |
| NMI No. V08/002389 | B1 | B2 | B4 | B1 | |
| NMI No. V08/002390 | B2 | B1 | B3 | B1 | B2 |
| *T. aureoviride* | | | | | |
| LU498 | B2 | B2 | C | A | |
| *T. koningii* | | | | | |
| LU506 | B2 | B2 | B4 | B3 | |
| LU507 | B4 | B3 | C | B3 | |
| LU508 | B3 | B3 | B4 | B3 | |
| LU509 | B3 | C | C | A | |
| LU566 | B4 | B4 | B4 | A | |
| LU713 | B1 | B2 | B3 | B3 | B2 |
| LU738 | B2 | B2 | B4 | B2 | B2 |
| *T. virens* | | | | | |
| LU540 | B1 | B1 | B2 | B4 | |
| LU547 | B1 | B1 | B1 | A | |
| LU549 | B1 | B1 | B4 | A | |
| LU555 | B1 | B1 | B4 | A | |
| *T. hamatum* | | | | | |
| LU565 | B3 | B3 | B4 | A | |
| LU592 | B3 | B2 | B4 | B4 | |
| LU593 | B3 | B3 | B4 | B3 | |
| LU594 | B4 | B3 | B4 | B4 | |
| LU595 | B2 | B2 | B4 | B3 | |
| LU740 | B2 | B2 | B4 | B3 | B2 |
| *T. harzianum* | | | | | |
| LU564 | B3 | B2 | B4 | A | |
| LU612 | B2 | B2 | B4 | A | |
| LU613 | B2 | B2 | B4 | A | |
| LU614 | B3 | B2 | B1 | A | |

TABLE 2-continued

Dual-plate assay screening of 102 *Trichoderma* isolates against soil-borne pasture pathogens. Isolates selected for further study are highlighted

| Isolates | KW11 | KW12 | KW13 | KW14 | KW15 |
|---|---|---|---|---|---|
| LU630 | B3 | B2 | B4 | A | A |
| LU631 | B3 | B2 | B4 | A | B4 |
| LU632 | B3 | B2 | B4 | A | A |
| LU635 | B2 | B2 | C | A | A |
| LU636 | B2 | B2 | B4 | A | C |
| LU637 | B2 | B3 | C | A | C |
| LU638 | B3 | B3 | B4 | A | B3 |
| LU639 | B3 | B2 | B4 | A | B2 |
| LU640 | B3 | B2 | B4 | A | B4 |
| LU641 | B2 | B1 | B4 | A | C |
| LU642 | B2 | B2 | B4 | A | B4 |
| LU643 | B2 | B2 | B4 | A | B4 |
| *T. viride* | | | | | |
| LU570 | B4 | B3 | C | B3 | |
| LU606 | B4 | B4 | B4 | B3 | |
| LU608 | B4 | B4 | B4 | B3 | |
| LU615 | B4 | B4 | B3 | B4 | |
| LU616 | B4 | B4 | B4 | B3 | B3 |
| LU618 | B4 | B3 | B4 | B3 | B4 |
| LU619 | B4 | B4 | B4 | B4 | B4 |
| LU620 | B2 | B1 | B4 | B1 | C |
| LU644 | B1 | B1 | B4 | B3 | D |
| LU645 | B1 | B2 | B4 | B2 | D |
| LU646 | B4 | B3 | B4 | B2 | B2 |
| LU647 | B1 | B4 | B4 | B3 | B1 |
| *T. fertile* | | | | | |
| LU609 | B2 | B4 | B4 | A | |
| LU610 | B2 | B4 | B4 | A | |
| LU611 | B2 | B4 | B2 | A | |
| LU622 | B3 | B3 | B4 | A | C |
| LU623 | B3 | D | B4 | A | D |
| *Trichoderma* spp. | | | | | |
| LU501 | B2 | B2 | C | A | |
| LU502 | B2 | B2 | C | A | |
| LU503 | B3 | B3 | C | A | |
| LU504 | B3 | B3 | C | A | |
| LU505 | B3 | B3 | C | A | |
| LU596 | B2 | B3 | B4 | B4 | |
| LU604 | B3 | B2 | D | B3 | |
| LU605 | B2 | B2 | D | B3 | |
| Apple orchard isolates | | | | | |
| KW1 | B3 | B3 | D | A | |
| KW2 | B4 | B4 | B4 | B4 | |
| KW3 | B2 | B2 | B4 | B3 | |
| KW4 | B4 | B2 | B4 | B2 | |
| KW5 | B3 | B2 | B4 | B3 | |
| KW6 | B4 | B4 | B4 | B3 | |
| KW7 | B2 | B2 | B4 | B3 | |
| KW8 | C | B4 | B4 | B4 | |
| KW9 | C | B3 | B4 | B1 | |
| Pasture isolates | | | | | |
| Ashley Dene | B2 | B2 | B4 | B3 | |
| Gorge | B2 | B3 | B4 | B3 | |
| Temuka | B4 | B4 | B4 | B4 | B4 |
| Paparua | B4 | B2 | B4 | B3 | B2 |
| Waimakariri | B4 | B4 | B4 | B4 | B4 |

Table 3

Pot Trial 1. Emergence, fresh shoot weight and dry root weight of perennial ryegrass (*Lolium perenne* cv. Embassy) plants grown in pathogen-free potting mix with various *Trichoderma* spp. isolates.

| Treatment | Emergence (%) | Shoot Weight (g) | Root Weight (g) |
|---|---|---|---|
| *T. virens* (LU540) | 77.5* | 7.55 | 4.21 |
| *T. virens* (LU547) | 81.3 | 11.22** | 5.41 |
| *T. atroviride* (LU634) | 73.1* | 9.13 | 5.86 |
| *T. atroviride* (LU644) | 75.6* | 8.81 | 4.42 |
| *T. koningii* (LU713) | 74.4* | 9.63 | 4.24 |
| *T. hamatum* (LU740) | 74.4* | 7.74 | 3.53 |
| *T. atroviride* (NMI No. V08/002388) | 77.5* | 8.19 | 5.02 |
| *T. atroviride* (NMI No. V08/002387) | 83.8 | 8.75 | 4.76 |
| *T. atroviride* (NMI No. V08/002389) | 87.5 | 22.92** | 7.97** |
| *T. atroviride* (NMI No. V08/002390) | 78.8 | 20.52** | 6.83** |
| Potting Mix control | 85.9 | 7.96 | 3.89 |
| LSD | 8.03 | 2.65 | 2.00 |

*Treatments with significantly lower values (P < 0.05) compared to Potting-mix control
**Treatments with significantly higher values (P < 0.05) compared to Potting-mix control

TABLE 4

Pot Trial 2. Emergence and fresh shoot weight of red clover (*Trifolium pratense* cv. Montgomery Red) plants grown in pathogen-free potting mix with various *Trichoderma* spp. isolates.

| Treatment | Emergence (%) | Shoot Weight (g) |
|---|---|---|
| *T. virens* (LU540) | 54.4 | 9.97 |
| *T. virens* (LU547) | 51.3* | 6.17*** |
| *T. atroviride* (LU634) | 60.0 | 8.63 |
| *T. atroviride* (LU644) | 56.9 | 10.33 |
| *T. koningii* (LU713) | 53.1 | 7.40 |
| *T. hamatum* (LU740) | 55.0 | 9.40 |
| *T. atroviride* (NMI No. V08/002388) | 54.4 | 8.79 |
| *T. atroviride* (NMI No. V08/002387) | 58.1 | 9.74 |
| *T. atroviride* (NMI No. V08/002389) | 58.8 | 12.24** |
| *T. atroviride* (NMI No. V08/002390) | 57.5 | 8.55 |
| Potting mix control | 58.4 | 8.77 |
| LSD | 6.36 | 1.87 |

*Treatments with significantly lower values (P > 0.05) compared to Potting-mix control
**Treatments with significantly higher values (P < 0.05) compared to Potting-mix control
***Treatments with significantly lower values (P < 0.05) compared to Potting-mix control

TABLE 5

Pot Trial 3. Effect of various *Trichoderma* spp. isolates on emergence, fresh shoot weight and dry toot weight of perennial ryegrass (*Lolium perenne* cv. Embassy) plants grown in potting mix containing *Rhizoctonia solani*.

| Treatment | Emergence (%) | Shoot Weight (g) | Root Weight (g) |
|---|---|---|---|
| Pathogen Control | 36.2 | 5.78 | 2.59 |
| *T. virens* (LU540) | 67.5** | 7.38 | 3.73 |
| *T. virens* (LU547) | 25.0 | 8.35 | 3.16 |
| *T. atroviride* (LU634) | 25.6 | 4.51 | 1.84 |
| *T. atroviride* (LU644) | 29.4 | 6.46 | 2.75 |
| *T. koningii* (LU713) | 10.0* | 1.95* | 0.79* |
| *T. hamatum* (LU740) | 6.2* | 2.08* | 0.55* |
| *T. atroviride* (NMI No. V08/002388) | 73.1** | 9.25** | 4.24** |
| *T. atroviride* (NMI No. V08/002387) | 69.4** | 8.13 | 3.17 |
| *T. atroviride* (NMI No. V08/002389) | 13.8* | 11.27** | 1.78 |
| *T. atroviride* (NMI No. V08/002390) | 15.6* | 15.76** | 2.98 |
| Potting Mix Control | 85.9** | 7.96 | 3.89 |
| LSD | 11.6 | 3.26 | 1.44 |

*Treatments with significantly lower values (P < 0.05) compared to pathogen control
**Treatments with significantly higher values (P < 0.05) compared to pathogen control

TABLE 6

Pot Trial 4. Effect of various *Trichoderma* spp. isolates on emergence, disease score and fresh shoot weight of red clover (*Trifolium pratense* cv. Montgomery Red) plants grown in potting mix containing *Sclerotinia trifoliorum*.

| Treatment | Emergence (%) | Disease Score (1-5 scale) | Shoot Weight (g) |
|---|---|---|---|
| Pathogen Control | 48.4 | 3.25 | 3.64 |
| *T. virens* (LU540) | 53.1 | 2.13** | 4.50 |
| *T. virens* (LU547) | 40.6 | 1.75** | 6.94* |
| *T. atroviride* (LU634) | 53.1 | 1.13** | 10.58* |
| *T. atroviride* (LU644) | 48.8 | 1.25** | 8.28* |
| *T. koningii* (LU713) | 51.2 | 2.25** | 6.25 |
| *T. hamatum* (LU740) | 56.9 | 1.06** | 11.57* |
| *T. atroviride* (NMI No. V08/002388) | 51.2 | 1.75** | 4.52 |
| *T. atroviride* (NMI No. V08/002387) | 53.8 | 1.13** | 7.86* |
| *T. atroviride* (NMI No. V08/002389) | 61.2* | 2.13** | 4.96 |
| *T. atroviride* (NMI No. V08/002390) | 42.5 | 2.00** | 4.98 |
| Potting Mix Control | 58.4 | 1.13** | 8.77 |
| LSD | 10.95 | 0.68 | 2.62 |

*Treatments with significantly higher values ($P < 0.05$) compared to pathogen control.
**Treatments with significantly lower disease scores ($P < 0.05$) compared to pathogen control.

TABLE 7

Pot Trial 5. Effect of various *Trichoderma* spp. isolates on emergence, percentage of sick plants, disease score and fresh shoot weight of white clover(*Trifolium repens* cv. Aran) plants grown in potting mix with *Pythium ultimum*.

| Treatment | Emergence (%) | Sick Plants$ (%) | Disease Score (1-5 scale) | Shoot Weight (g) |
|---|---|---|---|---|
| Pathogen Control | 58.8 | 68.4 | 3.30 | 3.16 |
| *T. virens* (LU540) | 61.0 | 53.5 | 2.90 | 3.92 |
| *T. virens* (LU547) | 67.2 | 36.1** | 2.88 | 5.03 |
| *T. atroviride* (LU634) | 64.5 | 36.0** | 2.13** | 6.37* |
| *T. atroviride* (LU644) | 69.0 | 43.3** | 2.80 | 4.44 |
| *T. koningii* (LU713) | 66.5 | 54.8 | 3.25 | 3.16 |
| *T. hamatum* (LU740) | 84.2* | 22.9** | 1.90** | 5.88 |
| *T. atroviride* (NMI No. V08/002388) | 61.2 | 55.1 | 3.00 | 3.82 |
| *T. atroviride* (NMI No. V08/002387) | 51.5 | 71.5 | 3.98 | 1.38 |
| *T. atroviride* (NMI No. V08/002389) | 71.2 | 41.7** | 3.15 | 3.07 |
| *T. atroviride* (NMI No. V08/002390) | 73.8 | 31.5** | 2.80 | 4.12 |
| Potting Mix Control | 88.5* | 0.0** | 1.08 | 11.89* |
| LSD | 15.1 | 24.1 | 0.92 | 2.93 |

$Percentage of sick plants out of the emerged seedlings.
*Treatments with significantly higher values ($P < 0.05$) compared to pathogen control.
**Treatments with significantly lower values ($P < 0.05$) compared to pathogen control.

Data for the deposited *Trichoderma atroviride* is usefully summarised in Table 8 below:

TABLE 8

Summary of growth promotion and disease control activity of six *Trichoderma* isolates in a range of pot trials.

| Isolate | Growth prom. | | Disease control | | |
|---|---|---|---|---|---|
| | p.r[1] | r.c[2] | R.s[3] | S.t[4] | P.u[5] |
| NMI V08/002388 | | | +++ | | |
| NMI V08/002387 | | | ++ | +++ | |
| NMI V08/002389 | +++[6] | ++ | + | | + |
| NMI V08/002390 | | | | ++ | + |

[1]perennial ryegrass,
[2]red clover,
[3]*Rhizoctonia solani*,
[4]*Sclerotinia trifoliorum*,
[5]*Pythium ultimum*
[6]+++ = high, ++ = medium, + = low Pot Trials Five glasshouse pot trials confirmed the disease control activity of different isolates towards the three pasture phytopathogens *R. solani*, *S. trifoliorum* and *P. ultimum* and demonstrated growth promotion of perennial ryegrass, red clover and white clover. Several isolates showed significant levels of disease control (Tables 4-8).

Conclusions

On the basis of these experiments four isolates (NMI No. V08/002388, NMI No. V08/002387, NMI No. V08/002389 and NMI No. V08/002390) were chosen for evaluation as Pasture Seed Additives. In addition to growth promotion and disease control capabilities, sporulation capability and compatibility with other *Trichoderma* isolates was used as selection criteria. *Trichoderma hamatum* LU740 was not chosen due to comparably low sporulation rates; *T. virens* LU547 was not chosen due to incompatibility with *T. atroviride* NMI No. V08/002389; *T. viride* LU644 was not chosen due to incompatibility with NMI No. V08/002388.

Example 2

*Trichoderma atroviride* (NMI No. V08/002388, NMI No. V08/002387, NMI No. V08/002389 and NMI No. V08/002390)

The *T. atroviride* strains were isolated from three separate locations in New Zealand. NMI No. V08/002388 and NMI No. V08/002387 were isolated from soil in Pukekohe, Auckland, New Zealand, respectively. NMI No. V08/002389 was isolated from a *Ciborinia camelliae* sclerotium from the Botanical gardens in Wellington, New Zealand. NMI No. V08/002390 was isolated from soil in Canterbury, New Zealand.

*Trichoderma atroviride* Identification

All *Trichoderma atroviride* isolates contained within the Pasture Seed Additive (PSA) were identified on the basis of taxonomic sequence analysis. According to the length and composition of the nucleotide sequences of the Internal Transcribed Spacer (ITS) region of the ribosomal gene cluster, the *T. atroviride* isolates are defined by 100% identity to the sequence AF456920 in the database GenBank (http://www.ncbi.nlm.nih.gov/) of the strain DAOM 222096.

Morphological Characteristics

All four *Trichoderma atroviride* isolates have the following morphological characteristics:
Mycelium: hyaline, smooth, septate
Colonies on agar: rapid growth—colony diameters are 5-8 cm after 4 days growth at 20° C. on malt-extract agar. Colonies produce a coconut odour which is indicative of 6-pentyl-alpha-pyrone production (an antibiotic).

Conidial Morphology of *Trichoderma atroviride*

Conidiation for all four *Trichoderma atroviride* appears granular or crusty in age; initially conidiation is colourless rapidly turning dark green. Conidia are produced from phialides and are dark-green and smooth walled (2.6-3.8×2.2-3.4 µM).

Example 3

A Preparation of *Trichoderma* spp. for Pot and Field Experiments

Storage cultures of conidia from *T. atroviride* isolates NMI No. V08/002388, NMI No. V08/002387, NMI No. V08/002389 and NMI No. V08/002390 were preserved in 20% glycerol at −80° C. until required.

In all pot trials, a mixture of 0.5% (w/w) wheat bran inoculum to potting-mix was used. Wheat bran inoculum was prepared as follows: A 1 L conical flask was ¼ filled with dry wheat bran and distilled water added to make it wet and then autoclaved at 121□C for 15 min at 15 p.s.i. The conical flasks were then inoculated with *Trichoderma* spp. agar plugs from the colony margin of 2 day old cultures grown on potato-dextrose agar (PDA) and incubated at 20° C. (12 h light/12 h dark) for 14 days. Flasks were thoroughly shaken every two days to produce uniform inoculum.

B Preparation of Composition

In all field trials, Pasture Seed Additive (PSA) was used as the Trichoderma inoculum. The composition was formulated by Agrimm Technologies Ltd., New Zealand and contains the four *T. atroviride* isolates of the invention with maize chip (greater than 85% w/w), diatomite, humate, clay acidulent, and a mix of nutrients containing soluble and insoluble carbohydrate, protein, fats and trace elements. PSA contains $10^{10}$ colony forming units (cfu) of *Trichoderma*/per kilogram and is formulated as a granule using standard mixing techniques in any appropriate rotary mixing bowl. The granules were mixed with the pasture seed and applied to pasture with standard grass seed drilling equipment.

Example 4

Pasture Seed Additive Field Trials

Introduction

Rapid growth of the daily industry over the last decade has seen an increase in intensified farming and a need for farmers to improve productivity. This study investigated the use of a *Trichoderma*-based biological product for the dairy industry which promotes improved seedling establishment along with improved yield and quality. On the basis of the results from Example 2, four isolates (NMI No. V08/002388, NMI No. V08/002387, NMI No. V08/002389 and NMI No. V08/002390) were selected for incorporation to the Trichoderma based product Pasture Seed Additive (PSA). PSA was formulated as per Example 3 by Agrimm Technologies for on farm testing to evaluate its potential as a biological product for dairy pasture improvement.

Methods

Field Trials

Field Trial 1—Doyleston

Field studies commenced in dairy pasture block at Doyleston, 15 km south of Christchurch, New Zealand. In Summer (December), the field was drilled with 25 kg/ha tetraploid perennial ryegrass (cv. Bealey), 2 kg/ha Timothy, 2 kg/ha white clover (cv. Huia) and 1 kg/ha Plantain. PSA was applied to half the block a rate of 30 kg/ha and the remaining half was left untreated.

Field Trial 2—Seafield Farm

The second field trial was done in a dairy pasture at Seafield, 70 km south of Christchurch, New Zealand. In Summer (December), the field was drilled with 12 kg/ha meadow fescue/Italian ryegrass cross (cv. Mt Ida), 13 kg/ha perennial ryegrass (cv. Sextant) and 3 kg/ha white clover (cv. Kopu II). PSA was applied to half the pasture at a rate of 28 kg/ha and the remaining half was left untreated. At the beginning of the second growing season (January 2008) 99% of the grass species had died due to unknown causes and white clover dominated the pasture. In April 2008 the field was sprayed with Pasture Guard MCPB to slow the clover growth and perennial ryegrass (cv. Quartet) was undersown at a rate of 17 kg/ha.

Field Trial 3—Lincoln University H2

The third field trial was done on a research field (H2) at Lincoln University, Christchurch, New Zealand. In Summer (December), the field was drilled with 28 kg/ha perennial ryegrass (cv. Bealey) and 2 kg/ha white clover (cv. Aran). Within the field 6 replicates of each treatment in 6 blocks were laid out. PSA was applied to the treatment blocks at a rate of 25 kg/ha and the control blocks were left untreated.

Field Trial 4—Lincoln University LUDF

The fourth field trial was done on the Lincoln University Dairy Farm (LUDF) at Lincoln University, Christchurch, New Zealand. In Spring (October), the field was drilled with 26 kg/ha perennial ryegrass (cv. Bealey), 2 kg/ha white clover (cv. Kotare) and 2 kg/ha white clover (cv. Sustain). Within the field 6 replicates of each treatment in 6 blocks were laid out. PSA was applied to the treatment blocks at a rate of 25 kg/ha and the control blocks were left untreated.

Seedling Emergence

Emerged plants were counted to assess germination in untreated control and pasture seed additive treated pasture. Sixteen random 0.2 m² quadrants were counted per treatment for seedling emergence. Mean % emergence was calculated based on the estimated number of seeds sown in 0.2 m²

Data Analysis

Results were analysed by applying a two sample t-test (An Introduction to Statistical Methods and Data Analysis by R. L. Ott and M. Longnecker, 5th Edition, 2001 published by Duxbury, a division of Thomson Learning, Inc.) to compare emergent plant numbers and % emergence between treatments.

Pasture Components

At variable intervals after sowing the dry weight of each pasture component was calculated. Pasture components were manually sampled from 8 random 0.2 m² quadrants per treatment and the dry weight of each component assessed.

Pasture Palatability

Palatability of the pasture from each faun trial was assessed using post grazing measurements with the rising plate meter. Post grazing measurements are indicative of where the cows have preferred to graze therefore leaving less residual pasture. Sixteen plate meter measurements were taken per treatment. Each measurement consisted of the mean of 20 plate meter readings. The mean of these readings was calculated to give residual pasture height (cm).

Data Analysis

Results were analysed by applying a two sample t-test to compare residual grazing heights between treatment areas.

Dry Matter Production

Pasture density was measured using a rising plate meter. This value is then converted to estimated Total Dry Matter production per hectare (kg/ha). Sixteen measurements were taken per treatment. Each measurement consisted of the mean of 20 plate meter readings. Plate meter readings are converted to dry matter (kg/ha) by calibrating the plate meter reading taken from a 0.2 m² quadrant with the cut, dried weight of the herbage from that same quadrant. A conversion factor is then applied to estimate the dry matter per hectare.

Data Analysis

Results were analysed by applying a two sample t-test to compare dry matter production between treatments.

Pasture Feed Quality

Pasture Feed Quality was measured by taking 12-20 cuttings of grass at grazing height (5 cm from ground) from random sites throughout each treatment area and either combining them into one sample bag per treatment or submitting the replicates as separate sample. Sample bags were sent to R J Hills Laboratories, Hamilton, New Zealand for analysis. The Pasture Feed Quality Test includes measurement of dry matter, crude protein, acid detergent fibre (ADF), neutral detergent fibre (NDF), digestibility (DOMD), and Metabolisable energy (ME). Some assessments also include analysis of essential minerals and elements. Where individual replicates were analysed the results are presented as mean values.

Results

Field Trial 1—Doyleston

Seedling Emergence

Addition of the PSA resulted in a significant increase in seedling emergence compared with the untreated controls for all components except plantain (Tables 9-10).

TABLE 9

Pasture emergence with mean number of plants/0.2 m²

| Treatment | Mean Numbers in 0.2 m² | | | |
|---|---|---|---|---|
| | Plantain | Clover | Ryegrass | Total |
| Control | 5.75 | 15.63 | 56.13 | 77.51 |
| PSA | 6.25 | *25.95 | *74.38 | *106.58 |
| % Increase in PSA | 9% | 66% | 32% | 37% |

*Indicates evidence of a significant increase in PSA treatment over control.

TABLE 10

Percent pasture emergence calculated from number of seeds sown/0.2 m²

| Treatment | % Emergence |
|---|---|
| Control | 38% |
| PSA | 53% |
| % Increase in PSA | 34% |

Pasture Components

Six months after sowing a significant increase in all pasture components, except plantain, was observed in the PSA treatments relative to the untreated control (Table 10).

TABLE 11

Mean dry weight of each plant component/0.2 m²

| Treatment | Mean Dry Weights (g) in 0.2 m² | | | |
|---|---|---|---|---|
| | Clover | Plantain | Ryegrass | Total |
| Control | 0.64 | 3.29 | 14.78 | 18.71 |
| PSA | 1.03 | 2.99 | *19.58 | *23.6 |
| % Inc in PSA | 61% | | 32% | 26% |

*Indicates evidence of a significant increase in PSA treatment over control.

Pasture Palatability

No significant increase in grazing intensity of PSA treatment over the control was observed (Table 12)

TABLE 12

Mean residual height of the post graze pasture. Palatability was measured after the first and the fifth grazes.

| Treatment | Residual Pasture Height (cm) | |
|---|---|---|
| | 1st Graze | 5th Graze |
| Control | 3.95 | 4.91 |
| PSA | 3.93 | 4.69 |

Dry Matter Production

The addition of PSA resulted in a significant increase in dry matter production which persisted throughout the course of the trial (Table 13).

TABLE 13

Dry matter pasture production in kg/ha between grazes from December 2006-September 2008

| Date of Pasture | Analysis | Control DM kg/ha | PSA DM kg/ha | Increase DM kg/ha | % Increase DM kg/ha |
|---|---|---|---|---|---|
| Dec. 12, 2006 | 1st Analysis | 1768 | *2011 | *243 | 13.7 |
| Jan. 9, 2007 | 2nd Analysis | 1960 | *2323 | *363 | 18.5 |
| Jan. 26, 2007 | 3rd Analysis | 1743 | *1905 | *162 | 9.3 |
| Mar. 12, 2007 | 4th Analysis | 1389 | *1512 | *123 | 8.8 |
| May 2, 2007 | 5th Analysis | 1064 | *1208 | *144 | 13.5 |
| Sep. 18, 2007 | 6th Anaylsis | 1502 | *1666 | *164 | 10.9 |
| Nov. 1, 2007 | 7th Analysis | 921.7 | 954.3 | 32.6 | 3.5 |
| Jan. 24, 2008 | 8th Analysis | 973.7 | *1022.9 | *49.2 | 5.1 |
| Feb. 27, 2008 | 9th Analysis | 768.8 | *820 | *51.2 | 6.7 |
| Apr. 7, 2008 | 10th Analysis | 1106 | 1104 | −2 | −0.2 |
| Sep. 29, 2008 | 11th Analysis | 1073 | *1224 | *151 | 14.1 |
| Totals | | 14269.2 | 1575.02 | 1481 | 10.4 |

*Indicates a significant increase in DM kg/ha production in PSA treatment over Control.

Pasture Feed Quality

A full analysis of pasture feed quality was conducted on pasture material harvested 3, 14 and 16 months after sowing (Tables 14-19).

TABLE 14

Pasture feed quality. Control block, Doyleston, December 2006.

Sample Name: Sunckell Control
Sample Type: Mixed Pasture, Dairy (P1)

| Analysis | | Level Found | Medium Range | Low | Medium | High |
|---|---|---|---|---|---|---|
| Dry Matter | (%) | 18.0 | 12.0-25.0 | | | |
| Crude Protein | (%) | 25.6 | 20.0-30.0 | | | |
| Acid Detergent Fibre | (%) | 20.4 | 20.0-30.0 | | | |
| Neutral Detergent Fibre | (%) | 33.3 | 30.0-45.0 | | | |
| Ash | (%) | 9.1 | 7.0-14.0 | | | |
| Digestibility (DOMD) | (%) | 81.3 | 65.0-80.0 | | | |
| Metabolisable Energy | (MJ/kg) | 13.5 | 9.0-12.0 | | | |

TABLE 15

Pasture feed quality. PSA treatment block, Doyleston, December 2006

Sample Name: Sunckell Control
Sample Type: Mixed Pasture, Dairy (P1)

| Analysis | | Level Found | Medium Range | Low | Medium | High |
|---|---|---|---|---|---|---|
| Dry Matter | (%) | 18.1 | 12.0-25.0 | | | |
| Crude Protein | (%) | 23.8 | 20.0-30.0 | | | |
| Acid Detergent Fibre | (%) | 19.2 | 20.0-30.0 | | | |
| Neutral Detergent Fibre | (%) | 31.3 | 30.0-45.0 | | | |
| Ash | (%) | 9.0 | 7.0-14.0 | | | |
| Digestibility (DOMD) | (%) | 80.8 | 65.0-80.0 | | | |
| Metabolisable Energy | (MJ/kg) | 13.4 | 9.0-12.0 | | | |

TABLE 16

Pasture feed quality. Control block, Doyleston, February 2008

Sample Name: Doyleston (Control)
Sample Type: Mixed Pasture, Dairy (P1)

| Analysis | | Level Found | Medium Range |
|---|---|---|---|
| Dry Matter | (%) | 15.5 | 12.0-25.0 |
| Crude Protein | (% DM) | 30.1 | 20.0-30.0 |
| Acid Detergent Fibre | (% DM) | 24.9 | 20.0-30.0 |
| Neutral Detergent Fibre | (% DM) | 40.0 | 30.0-45.0 |
| Ash | (% DM) | 12.0 | 7.0-14.0 |
| Digestibility (DOMD) | (%) | 73.0 | 65.0-80.0 |
| Metabolisable Energy | (MJ/kg) | 11.7 | 9.0-12.0 |

TABLE 17

Pasture feed quality. PSA treatment block, Doyleston, February 2008

Sample Name: Doyleston (PSA)
Sample Type: Mixed Pasture, Dairy (P1)

| Analysis | | Level Found | Medium Range |
|---|---|---|---|
| Dry Matter | (%) | 14.7 | 12.0-25.0 |
| Crude Protein | (% DM) | 31.1 | 20.0-30.0 |
| Acid Detergent Fibre | (% DM) | 24.2 | 20.0-30.0 |
| Neutral Detergent Fibre | (% DM) | 36.6 | 30.0-45.0 |
| Ash | (% DM) | 12.1 | 7.0-14.0 |
| Digestibility (DOMD) | (%) | 75.4 | 65.0-80.0 |
| Metabolisable Energy | (MJ/kg) | 12.1 | 9.0-12.0 |

TABLE 18

Pasture feed quality. Control block, Doyleston, April 2008

Sample Name: Doyleston (Control)
Sample Type: Mixed Pasture, Dairy (P1)

| Analysis | | Level Found | Medium Range |
|---|---|---|---|
| Nitrogen | (%) | 3.2 | 4.0-5.0 |
| Phosphorus | (%) | 0.33 | 0.38-0.45 |
| Potassium | (%) | 3.0 | 2.5-3.0 |
| Sulphur | (%) | 0.36 | 0.30-0.40 |
| Calcium | (%) | 0.70 | 0.60-1.00 |
| Magnesium | (%) | 0.20 | 0.20-0.30 |
| Sodium | (%) | 0.73 | 0.15-0.30 |
| Iron | (mg/kg) | 98 | 100-250 |
| Manganese | (mg/kg) | 56 | 60-150 |
| Zinc | (mg/kg) | 25 | 30-50 |
| Copper | (mg/kg) | 9 | 10-12 |
| Boron | (mg/kg) | 8 | 10-15 |

TABLE 18-continued

Pasture feed quality. Control block, Doyleston, April 2008

| Molybdenum | (mg/kg) | 0.67 | 0.50-1.2 |
| --- | --- | --- | --- |
| Cobalt | (mg/kg) | 0.04 | 0.10-0.20 |
| Selenium | (mg/kg) | 0.06 | 0.08-0.15 |
| Chloride | (%) | 1.4 | 0.30-2.4 |
| Dry Matter | (%) | 16.6 | 12.0-25.0 |
| Crude Protein | (% DM) | 21.1 | 20.0-30.0 |
| Acid Detergent Fibre | (% DM) | 23.5 | 20.0-30.0 |
| Neutral Detergent Fibre | (% DM) | 39.1 | 30.0-45.0 |
| Ash | (% DM) | 10.8 | 7.0-14.0 |
| Digestibility (DOMD) | (%) | 77.1 | 65.0-80.0 |
| Metabolisable Energy | (MJ/kg) | 12.3 | 9.0-12.0 |

TABLE 19

Pasture feed quality. PSA treatment block, Doyleston, April 2008

Sample Name: Doyleston (PSA)
Sample Type: Mixed Pasture, Dairy (P1)

| Analysis | | Level Found | Medium Range |
| --- | --- | --- | --- |
| Nitrogen | (%) | 3.2 | 4.0-5.0 |
| Phosphorus | (%) | 0.35 | 0.38-0.45 |
| Potassium | (%) | 2.7 | 2.5-3.0 |
| Sulphur | (%) | 0.33 | 0.30-0.40 |
| Calcium | (%) | 0.74 | 0.60-1.00 |
| Magnesium | (%) | 0.20 | 0.20-0.30 |
| Sodium | (%) | 0.82 | 0.15-0.30 |
| Iron | (mg/kg) | 114 | 100-250 |
| Manganese | (mg/kg) | 52 | 60-150 |
| Zinc | (mg/kg) | 27 | 30-50 |
| Copper | (mg/kg) | 11 | 10-12 |
| Boron | (mg/kg) | 9 | 10-15 |
| Molybdenum | (mg/kg) | 0.71 | 0.50-1.2 |
| Cobalt | (mg/kg) | 0.05 | 0.10-0.20 |
| Selenium | (mg/kg) | 0.04 | 0.08-0.15 |
| Chloride | (%) | 1.5 | 0.30-2.4 |
| Dry Matter | (%) | 15.5 | 12.0-25.0 |
| Crude Protein | (% DM) | 20.8 | 20.0-30.0 |
| Acid Detergent Fibre | (% DM) | 24.1 | 20.0-30.0 |
| Neutral Detergent Fibre | (% DM) | 40.4 | 30.0-45.0 |
| Ash | (% DM) | 10.7 | 7.0-14.0 |
| Digestibility (DOMD) | (%) | 76.9 | 65.0-80.0 |
| Metabolisable Energy | (MJ/kg) | 12.3 | 9.0-12.0 |

Field Trial 2—Seafield

Seedling Emergence

Addition of the PSA resulted in a significant decrease in seedling emergence compared with the untreated controls for all components. NIWA weather information and farm records show that the PSA treated pasture alone received irrigation and 12 mm of rain on the same day. This, and the resulting cooling of the soil, may have delayed seedling emergence. (Tables 20-21).

TABLE 20

Pasture emergence with mean number of plants/0.2 m²

| | Mean Numbers in a 0.2 m² | | |
|---|---|---|---|
| Treatment | Clover | Ryegrass | Total |
| Control | 22.9 | 143.2 | 166.1 |
| PSA | ^12.6 | ^93.3 | 105.9 |
| % Decrease in PSA | 45% | 35% | 36% |

^Indicates evidence of a significant decrease in PSA treatment over Control.

TABLE 21

Percent seedling emergence calculated from number of seeds sown in a 0.2 m² plot.

| Treatment | % Emergence |
|---|---|
| Control | 83% |
| PSA | 53% |
| % Decrease in PSA | 30% |

Pasture Components

Four months after sowing a significant increase in the ryegrass component was observed in the PSA treatments relative to the untreated control (Table 22).

TABLE 22

Mean dry weight of each plant component/0.2 m²

| | Mean Dry Weights (g) in 0.2 m² | | |
|---|---|---|---|
| Treatment | Clover | Ryegrass | Total |
| Control | 0.6853 | 14.21 | 14.9 |
| PSA | 0.4581 | *18.46 | *18.9 |
| % Increase in PSA | | 30% | 27% |

*Indicates evidence of a significant increase in PSA treatment compared to control.

Pasture Palatability

A significant increase in grazing intensity of PSA treatment over the control was observed after the fifth graze (Table 23).

TABLE 23

Mean residual height of the post graze pasture. Palatability was measured after the first and the fifth grazes.

| | Residual Pasture Height (cm) | |
|---|---|---|
| Treatment | 1st Graze | 5th Graze |
| Control | 4.62 | 3.28 |
| PSA | 4.39 | *2.89 |
| % Increase in Grazing on PSA | 5% | 12% |

*Indicates a significant decrease in residual height of the pasture indicating an increase in grazing of PSA treated pasture over control.

Dry Matter Production

The addition of PSA resulted in an overall increase in dry matter production, which persisted after the field was undersown. (Tables 24-25).

TABLE 24

Dry matter pasture production in kg/ha between grazes from December 2006-February 2008

| Date of Pasture | Analysis | Control DM kg/ha | PSA DM kg/ha | Increase DM kg/ha | % Increase DM kg/ha |
|---|---|---|---|---|---|
| Dec. 12, 2006 | 1st Analysis | 1220 | 1128 | −92 | −7.5 |
| Jan. 19, 2007 | 2nd Analysis | 1218 | *1405 | *187 | 15.4 |
| Jan. 27, 2007 | 3rd Analysis | 1742 | *2067 | *325 | 18.7 |
| Feb. 14, 2007 | 4th Analysis | 1045 | *1141 | *96 | 9.0 |
| Apr. 20, 2007 | 5th Analysis | 828 | *887 | *59 | 7.1 |
| May 29, 2007 | 6th Analysis | 698 | *836 | *138 | 19.8 |
| Aug. 20, 2007 | 7th Analysis | 1216 | 1264 | 48 | 4.0 |
| Oct. 30, 2007 | 9th Analysis | 1042 | 1096 | 54 | 5.2 |
| Jan. 29, 2008 | 10th Analysis | 1066 | 1059 | −7 | −0.7 |
| Feb. 29, 2008 | 11th Analysis | 1175 | 1166 | −9 | −0.8 |
| Totals | | 11250 | 12049 | 799 | 7.1 |

*Indicates a significant increase in DM kg/ha production in PSA treatment over Control.

TABLE 25

Dry matter pasture production on undersown pasture in kg/ha between grazes from September 2008-October 2008

| Date of Pasture | Analysis | Control DM kg/ha | PSA DM kg/ha | Increase DM kg/ha | % Increase DM kg/ha |
|---|---|---|---|---|---|
| Sep. 19, 2008 | 1st Analysis | 1801 | 1821 | 20 | 1.1 |
| Oct. 17, 2008 | 2nd Analysis | 1256 | *1338.9 | *82.9 | 6.6 |
| Totals | | 3057 | 3159.9 | 102.9 | 3.4 |

*Indicates a significant increase in DM kg/ha production in PSA treatment over Control.

Pasture Feed Quality

A full analysis of pasture feed quality was conducted on pasture material harvested 2 months and 6 months after sowing (Tables 26-29).

TABLE 26

Pasture feed quality. Control block, Seafield, December 2006.

| Sample Name: | Mc Gregor Control | | | | | |
|---|---|---|---|---|---|---|
| Sample Type: | Mixed Pasture, Dairy (P1) | | | | | |
| Analysis | | Level Found | Medium Range | Low | Medium | High |
| Dry Matter | (%) | 14.0 | 12.0-25.0 | | | |
| Crude Protein | (%) | 29.6 | 20.0-30.0 | | | |
| Acid Detergent Fibre | (%) | 17.0 | 20.0-30.0 | | | |
| Neutral Detergent Fibre | (%) | 30.7 | 30.0-45.0 | | | |
| Ash | (%) | 9.3 | 7.0-14.0 | | | |
| Digestibility (DOMD) | (%) | 82.4 | 65.0-80.0 | | | |
| Metabolisable Energy | (MJ/kg) | 13.7 | 9.0-12.0 | | | |

TABLE 27

Pasture feed quality. PSA treatment block, Seafield, December 2006 (Summer).

| Sample Name: | Mc Gregor Test | | | | | |
|---|---|---|---|---|---|---|
| Sample Type: | Mixed Pasture, Dairy (P1) | | | | | |
| Analysis | | Level Found | Medium Range | Low | Medium | High |
| Dry Matter | (%) | 13.4 | 12.0-25.0 | | | |
| Crude Protein | (%) | 34.1 | 20.0-30.0 | | | |
| Acid Detergent Fibre | (%) | 16.1 | 20.0-30.0 | | | |
| Neutral Detergent Fibre | (%) | 29.9 | 30.0-45.0 | | | |
| Ash | (%) | 8.8 | 7.0-14.0 | | | |
| Digestibility (DOMD) | (%) | 83.0 | 65.0-80.0 | | | |
| Metabolisable Energy | (MJ/kg) | 13.8 | 9.0-12.0 | | | |

TABLE 28

Pasture feed quality. Control block, Seafield, April 2007 (Autumn).

| Sample Name: | Seafield Control | | | | | |
|---|---|---|---|---|---|---|
| Sample Type: | Mixed Pasture, Dairy (P1) | | | | | |
| Analysis | | Level Found | Medium Range | Low | Medium | High |
| Nitrogen | (%) | 4.7 | 4.0-5.0 | | | |
| Phosphorus | (%) | 0.54 | 0.35-0.45 | | | |
| Potassium | (%) | 3.9 | 2.5-3.0 | | | |
| Sulphur | (%) | 0.46 | 0.30-0.40 | | | |
| Calcium | (%) | 0.77 | 0.45-1.00 | | | |
| Magnesium | (%) | 0.31 | 0.20-0.25 | | | |
| Sodium | (%) | 0.45 | 0.15-0.25 | | | |
| Iron | (mg/kg) | 225 | 100-250 | | | |
| Manganese | (mg/kg) | 84 | 40-150 | | | |

TABLE 28-continued

Pasture feed quality. Control block, Seafield, April 2007 (Autumn).

| Analysis | | Level Found | Medium Range |
|---|---|---|---|
| Zinc | (mg/kg) | 31 | 30-50 |
| Copper | (mg/kg) | 11 | 9-12 |
| Boron | (mg/kg) | 8 | 10-15 |
| Dry Matter | (%) | 13.7 | 12.0-25.0 |
| Crude Protein | (%) | 29.2 | 20.0-30.0 |
| Acid Detergent Fibre | (%) | 22.3 | 20.0-30.0 |
| Neutral Detergent Fibre | (%) | 36.0 | 30.0-45.0 |
| Ash | (% | 10.7 | 7.0-14.0 |
| Digestibility (DOMD) | (%) | 67.0 | 65.0-80.0 |
| Metabolisable Energy | (MJ/kg) | 10.6 | 9.0-12.0 |

TABLE 29

Pasture feed quality. PSA treatment block, Seafield, April 2007 (Autumn).

Sample Name: Seafield Test
Sample Type: Mixed Pasture, Dairy (P1)

| Analysis | | Level Found | Medium Range |
|---|---|---|---|
| Nitrogen | (%) | 4.7 | 4.0-5.0 |
| Phosphorus | (%) | 0.54 | 0.35-0.45 |
| Potassium | (%) | 3.4 | 2.5-3.0 |
| Sulphur | (%) | 0.44 | 0.30-0.40 |
| Calcium | (%) | 0.71 | 0.45-1.00 |
| Magnesium | (%) | 0.28 | 0.20-0.25 |
| Sodium | (%) | 0.43 | 0.15-0.25 |
| Iron | (mg/kg) | 234 | 100-250 |
| Manganese | (mg/kg) | 74 | 40-150 |
| Zinc | (mg/kg) | 27 | 30-50 |
| Copper | (mg/kg) | 10 | 9-12 |
| Boron | (mg/kg) | 9 | 10-15 |
| Dry Matter | (%) | 14.9 | 12.0-25.0 |
| Crude Protein | (%) | 29.1 | 20.0-30.0 |
| Acid Detergent Fibre | (%) | 21.5 | 20.0-30.0 |
| Neutral Detergent Fibre | (%) | 33.6 | 30.0-45.0 |
| Ash | (% | 10.5 | 7.0-14.0 |
| Digestibility (DOMD) | (%) | 67.9 | 65.0-80.0 |
| Metabolisable Energy | (MJ/kg) | 10.8 | 9.0-12.0 |

Field Trial 3—Lincoln University H2

Seedling Emergence

Addition of the PSA resulted in a significant increase in ryegrass emergence compared with the untreated controls (Tables 30-31).

TABLE 30

Pasture emergence with mean number of plants/0.2 m$^2$

| | Mean Numbers in 0.2 m$^2$ | | |
|---|---|---|---|
| Treatment | Clover | Ryegrass | Total |
| Control | 7.7 | 84.7 | 92.4 |
| PSA | 7.3 | *104.3 | 111.6 |
| % Increase in PSA | | 23% | 20% |

*Indicates a significant increase in PSA treatment over Control.

TABLE 31

Percent pasture emergence calculated from number of seeds sown/0.2 m².

| Treatment | % Emergence |
|---|---|
| Control | 46% |
| PSA | 56% |
| % Increase in PSA | 21.7% |

Dry Matter Production

The addition of PSA resulted in an initial significant increase in dry matter production (Table 32).

TABLE 32

Dry matter pasture production in kg/ha between grazes from April 2007-October 2008

| Date of Pasture | Analysis | Control DM kg/ha | PSA DM kg/ha | Increase DM kg/ha | % Increase DM kg/ha |
|---|---|---|---|---|---|
| Apr. 3, 2007 | 1st Analysis | 1714 | *2251 | *537 | 31.3 |
| May 8, 2007 | 2nd Analysis | 1298 | *1529 | *231 | 17.8 |
| Jun. 14, 2007 | 3rd Analysis | 3277 | 3366 | 89 | 2.7 |
| Oct. 5, 2007 | 4th Analysis | 2773 | 2966 | 193 | 7.0 |
| Nov. 12, 2007 | 5th Analysis | 1505 | 1519 | 14 | 0.9 |
| Dec. 17, 2007 | 6th Analysis | 2258 | 2277 | 19 | 0.8 |
| Mar. 7 2008 | 7th Analysis | 2230 | 2056 | −174 | −7.8 |
| May 14, 2008 | 8th Analysis | 1606 | 1575 | −31 | −1.9 |
| Jun. 5, 2008 | 9th Analysis | 1897.8 | 2010 | 112.2 | 5.9 |
| Sep. 12, 2008 | 10th Analysis | 966 | 1023 | 57 | 5.9 |
| Oct. 31, 2008 | 11th Analysis | 2594 | 2690 | 96 | 3.7 |
| Totals | | 22118.8 | 23262 | 1143.2 | 5.2 |

*Indicates a significant increase in DM kg/ha production in PSA treatment over Control.

Pasture Feed Quality

A full analysis of pasture feed quality was conducted on pasture material harvested 3, 5, 9 and 21 months after sowing (Tables 33-37).

TABLE 33

Pasture feed quality. Control block, Lincoln University H2, April 2007 (Autumn).

| Sample Name: | H2 Control | |
|---|---|---|
| Sample Type: | Mixed Pasture, Dairy (P1) | |
| Analysis | | Level Found | Medium Range |

| Analysis | | Level Found | Medium Range |
|---|---|---|---|
| Dry Matter | (%) | 12.7 | 12.0-25.0 |
| Crude Protein | (%) | 29.5 | 20.0-30.0 |
| Acid Detergent Fibre | (%) | 21.5 | 20.0-30.0 |
| Neutral Detergent Fibre | (%) | 35.8 | 30.0-45.0 |
| Ash | (%) | 11.1 | 7.0-14.0 |
| Digestibility (DOMD) | (%) | 76.9 | 65.0-80.0 |
| Metabolisable Energy | (MJ/kg) | 12.6 | 9.0-12.0 |

TABLE 34

Pasture feed quality. PSA treatment block, Lincoln University H2, April 2007 (Autumn).

| Sample Name: | H2 PSA | |
|---|---|---|
| Sample Type: | Mixed Pasture, Dairy (P1) | |

| Analysis | | Level Found | Medium Range |
|---|---|---|---|
| Dry Matter | (%) | 12.7 | 12.0-25.0 |
| Crude Protein | (%) | 28.0 | 20.0-30.0 |
| Acid Detergent Fibre | (%) | 21.5 | 20.0-30.0 |
| Neutral Detergent Fibre | (%) | 36.9 | 30.0-45.0 |
| Ash | (%) | 10.0 | 7.0-14.0 |
| Digestibility (DOMD) | (%) | 75.6 | 65.0-80.0 |
| Metabolisable Energy | (MJ/kg) | 12.4 | 9.0-12.0 |

TABLE 35

Pasture feed quality. Control block, Lincoln University H2, June 2007 (Winter).

Sample Name: Treatment 4
Sample Type: Mixed Pasture, Dairy (P1)

| Analysis | | Level Found | Medium Range |
|---|---|---|---|
| Dry Matter | (%) | 12.2 | 12.0-25.0 |
| Crude Protein | (%) | 24.2 | 20.0-30.0 |
| Acid Detergent Fibre | (%) | 24.1 | 20.0-30.0 |
| Neutral Detergent Fibre | (%) | 43.1 | 30.0-45.0 |
| Ash | (%) | 11.8 | 7.0-14.0 |
| Digestibility (DOMD) | (%) | 77.7 | 65.0-80.0 |
| Metabolisable Energy | (MJ/kg) | 12.8 | 9.0-12.0 |

TABLE 36

Pasture feed quality. PSA treatment block, Lincoln University H2, June 2007 (Winter).

Sample Name: Treatment 5
Sample Type: Mixed Pasture, Dairy (P1)

| Analysis | | Level Found | Medium Range |
|---|---|---|---|
| Dry Matter | (%) | 12.5 | 12.0-25.0 |
| Crude Protein | (%) | 26.5 | 20.0-30.0 |
| Acid Detergent Fibre | (%) | 21.5 | 20.0-30.0 |
| Neutral Detergent Fibre | (%) | 41.2 | 30.0-45.0 |
| Ash | (%) | 10.1 | 7.0-14.0 |
| Digestibility (DOMD) | (%) | 78.6 | 65.0-80.0 |
| Metabolisable Energy | (MJ/kg) | 13.0 | 9.0-12.0 |

TABLE 37

Pasture feed quality Lincoln University H2.
Results represent the mean values from replicate samples.

| Analysis | | 1 Oct. 2007 | | 30 Oct. 2008 | |
|---|---|---|---|---|---|
| | | Control | PSA | Control | PSA |
| Dry matter | (%) | 17 | 17.25 | 17.65 | 17.5 |
| Crude Protein | (%) | 16.68 | 16.25 | 20.55 | 20.55 |
| Acid Detergent Fibre | (%) | 21.983 | 21.2 | 22.55 | 22.05 |
| Neutral Detergent Fibre | (%) | 37.47 | 36.65 | 34.7 | 33.95 |
| Ash | (%) | 9.333 | 8.933 | 9 | 8.75 |
| Digestibility (DOMD) | (%) | 78.28 | 79.17 | 78.3 | 78.85 |
| Metabolisable Energy | (MJ/kg) | 12.517 | 12.65 | 12.55 | 12.65 |

Field Trial 4—Lincoln University LUDF

Seedling Emergence

Addition of the PSA resulted in a significant increase in clover emergence compared with the untreated control (Tables 38-39).

TABLE 38

Pasture emergence with mean number of plants/0.2 m$^2$

| | Mean Numbers in 0.2 m$^2$ | | |
|---|---|---|---|
| Treatment | Clover | Ryegrass | Total |
| Control | 32 | 155.5 | 187.5 |
| PSA | *52.88 | 128.5 | 181.38 |
| % Increase in PSA | 65.25 | | |

*Indicates a significant increase in PSA treatment over Control.

TABLE 39

Percent pasture emergence calculated from number of seeds sown/0.2 m$^2$.

| Treatment | % Emergence |
|---|---|
| Control | 68.2 |
| PSA | 66.0 |

Dry Matter Production

The addition of PSA resulted in an initial significant increase in dry matter production (Table 40).

TABLE 40

Dry matter pasture production in kg/ha between grazes from January 2008-May 2008

| Date of Pasture | Analysis | Control DM kg/ha | PSA DM kg/ha | Increase DM kg/ha | % Increase DM kg/ha |
|---|---|---|---|---|---|
| Jan. 25, 2008 | 1st Analysis | 971 | *1209 | *238 | 24.5 |
| Feb. 11, 2008 | 2nd Analysis | 910 | 1042 | 132 | 14.5 |
| Mar. 5, 2008 | 3rd Analysis | 1147 | 1247 | 100 | 8.7 |
| Apr. 9, 2008 | 4th Analysis | 1166 | 1195 | 29 | 2.5 |
| May 19, 2008 | 5th Analysis | 1108 | 1182 | 74 | 6.7 |
| Totals | | 5302 | 5875 | 573 | 10.81 |

*Indicates a significant increase in DM kg/ha production in PSA treatment over Control.

Pasture Feed Quality

A full analysis of pasture feed quality was conducted on pasture material harvested 4 and 15 months after sowing (Table 41).

TABLE 41

Pasture feed quality Lincoln University LUDF. Results represent the mean values from replicate samples.

| Analysis | | 11 Feb. 2007 | | 15 Jan. 2008 | |
|---|---|---|---|---|---|
| | | Control | PSA | Control | PSA |
| Dry matter | (%) | 13.15 | 12.55 | 14.67 | 14.82 |
| Crude Protein | (%) | 30.1 | 29.2 | 31.87 | 29.73 |
| Acid Detergent Fibre | (%) | 23.75 | 24.1 | 24 | 24.3 |
| Neutral Detergent Fibre | (%) | 42.2 | 41.65 | 42.75 | 42.87 |
| Ash | (%) | 12.2 | 12.15 | 12.37 | 12.5 |
| Digestibility (DOMD) | (%) | 74.55 | 75.35 | 73.2 | 73.33 |
| Metabolisable Energy | (MJ/kg) | 11.95 | 12.05 | 11.7 | 11.75 |

Conclusions

Two dairy farm trials and two research farm trials conducted over the past 30 months have successfully shown that seedling establishment and dairy pasture growth is significantly improved with the biological product Pasture Seed Additive (PSA).

Basic feed profile tests include: dry matter, crude protein, ash, acid detergent fibre, neutral detergent fibre, digestibility and metabolisable energy. These feed components are interlinked, an increase in one component results in the decrease in another component. An ideal feed sample must be high in dry matter, digestibility, metabolisable energy and low in ash, crude protein, neutral detergent fibre, acid detergent fibre. Pasture grown using the PSA compositions of the invention also exhibited these desirable properties.

It will be appreciated that the above description is provided by way of example only and that variations in both the materials and techniques used which are known to those persons skilled in the art are contemplated.

C. Additional Indications

Australia

The applicant hereby gives notice that the furnishing of a sample of a microorganism shall only be effected prior to grant of a patent, or prior to the lapsing, refusal or withdrawal of the application, to a person who is a skilled addressee without an interest in the invention (Regulation 3.25(3) of the Australian Patents Regulations.

Canada

The applicant hereby requests that, until either a Canadian patent has been issued on the basis of the application or the application has been refused or abandoned and no longer subject to reinstatement, or is withdrawn, the furnishing of a sample of deposited biological material referred to in the application only be effected to an independent expert nominated by the Commissioner of Patents.

Croatia

The applicant hereby requests that the samples, upon request, be made available between the publication of the application and the granting of the patent to anyone requesting them, or, if the applicant so requests, only to an independent expert, or to, after the patent has been granted, and notwithstanding cancellation or revocation of the patent, anyone requesting them.

Denmark

The applicant hereby requests that, until the application has been laid open to public inspection (by the Danish Patent and Trademark Office), or has been finally decided upon by the Danish Patent and Trademark Office without having been laid open to public inspection, the furnishing of a sample shall only be effected to an expert in the art.

European Patent

In respect of those designations in which a European Patent is sought a sample of the deposited microorganism will be made available until the publication of the mention of the grant of the European patent or until the date on which the application has been refused or withdrawn or is deemed to be withdrawn, only by the issue of such a sample to an expert nominated by the person requesting the sample (Rule 28(4) EPC).

Finland

The applicant hereby requests that, until the application has been laid open to public inspection (by the National Board of Patents and Registration), or has been finally decided upon by the National Board of Patents and Registration without having been laid open to public inspection, the furnishing of a sample shall only be effected to an expert in the art.

France

The applicant hereby requests that, until the publication of the grant of the patent, the withdrawal or refusal of the application, the deposited culture shall only be accessible to an expert designated by the applicant.

Iceland

The applicant hereby requests that, until a patent has been granted or a final decision taken by the Icelandic Patent Office concerning the application which has not resulted in a patent, the furnishing of a sample shall only be effected to an expert in the art.

Ireland

The applicant hereby requests that, until the preparations for publication of the patent application have been completed by the Comptroller, a sample of the microorganism should be made available only to an expert.

Netherlands

The applicant hereby requests that until the date of grant of a patent or date on which the application is refused or withdrawn or lapsed, the microorganism shall be made available as provided in Rule 31F(1) of the Patent Rules only by issue of a sample to an expert.

Norway

The applicant hereby requests that, until the application has been laid open to public inspection (by the Norwegian Patent Office), or has been finally decided upon by the Norwegian Patent Office without having been laid open to public inspection, the furnishing of a sample shall only be effected to an expert in the art.

Singapore

The applicant hereby requests that the furnishing of a sample of a microorganism shall only be made available to an expert.

Spain

The applicant hereby requests that until the date of grant of a patent or date on which the application is refused or withdrawn or lapsed, the biological material shall be made available as provided in Article 45 SPL only by issue of a sample to an expert.

Sweden

The applicant hereby requests that, until the application has been laid open for public inspection (by the Swedish Patent Office), or has been finally decided upon by the Swedish Patent Office without having been laid open to public inspection, the furnishing of a sample shall only be effected to an expert in the art.

United Kingdom

The applicant hereby requests that the furnishing of a sample of a microorganism shall only be made available to an expert.

Other Nominated Designations

Where such provisions exist, the applicant hereby requests that, until the publication or grant of a patent, the withdrawal or refusal of the application, the deposited culture shall only be effected to an expert in the art.

I claim:

1. A composition comprising, in a reproductively viable form and amount, each of the following strains:
   (a) *Trichoderma atroviride* NMI No. V08/002387;
   (b) *Trichoderma atroviride* NMI No. V08/002389;
   (c) *Trichoderma atroviride* NMI No. V08/002390; and
   (d) *Trichoderma atroviride* NMI No. V08/002388;
and an agriculturally acceptable carrier, diluent or adjuvant.

2. A composition comprising in a reproductively viable form and amount, (i) at least one strain of *Trichoderma atroviride* selected from:
   (a) *Trichoderma atroviride* NMI No. V08/002387;
   (b) *Trichoderma atroviride* NMI No. V08/002389; and
   (c) *Trichoderma atroviride* NMI No. V08/002390; or
   (ii) all of strains (a), (b) and (c)
and an agriculturally acceptable carrier, diluent or adjuvant.

3. A composition according to claim 2 which further comprises *Trichoderma atroviride* NMI No. V08/002388 in a reproductively viable form and amount.

4. A composition according to claim 2 which is effective against one or more soil borne plant pathogens.

5. A composition according to claim 4 wherein the soil borne plant pathogens are selected from *Rhizoctonia, Sclerotinia, Pythium*, and *Fusarium*.

6. A composition according to claim 2 wherein the strain(s) are present in the form of reproductively viable spores.

7. A composition according to claim 6 wherein the spores are present in a concentration range of from about $1 \times 10^3$ to $1 \times 10^{14}$ CFU per gram or millilitre, or $1 \times 10^6$ to $1 \times 10^{11}$, or $1 \times 10^5$, $1 \times 10^8$, or $1 \times 10^6$ to $1 \times 10^7$ CFU/g or ml.

8. A composition according to claim 2 which is formulated as a seed coating, or is in the form of a pellet or prill.

9. A composition according to claim 2 which is:
   (a) a biological control composition, or
   (b) a plant growth promoter composition, or
   (c) both (a) and (b).

10. A seed coated with a composition according to claim 2.

11. A biologically pure culture of a *Trichoderma atroviride* strain selected from the strains on deposit at National Measurement Institute, Pymble, Australia, under accession Nos. NMI V08/002387, NMI VO8/002389 and NMI VO8/002390.

12. A method for controlling soil borne plant pathogens on a seed or plant, or in soil, pasture or turf, the method comprising applying to said seed, plant, soil, pasture or turf, a composition according to claim 2, or one or more *T. atroviride* selected from *T. atroviride* Nos. NMI V08/002387, NMI V08/002388, NMI V08/002389, and NMI V08/002390.

13. A method according to claim 12 wherein the pathogen is a *Rhizoctonia, Sclerotinia, Pythium*, or *Fusarium*.

14. A method for increasing plant yield, the method comprising applying to a seed, plant or pasture, turf, or soil, a composition according to claim 2, or one or more *T. atroviride* selected from *T. atroviride* Nos. NMI V08/002387, NMI V08/002388, NMI V08/002389, and NMI V08/002390.

15. A method according to claim 14 wherein a mixture of two, three or four *T. atroviride* is applied.

16. A method according to claim 12 wherein the seed or plant is a pasture, grass, or turf grass, seed or plant.

17. A method according to claim 14 wherein the seed or plant is a pasture, grass, or turf grass, seed or plant.

18. A method according to claim 16 wherein the pasture plant is ryegrass or clover or a mixture thereof.

19. A method according to claim 17 wherein the pasture plant is ryegrass or clover or a mixture thereof.

20. A method according to claim 12 wherein a mixture of two, three or four *T. atroviride* is applied.

* * * * *